(12) United States Patent
Mack et al.

(10) Patent No.: US 9,938,343 B2
(45) Date of Patent: Apr. 10, 2018

(54) DIAGNOSTIC METHOD FOR DETERMINING THE PRESENCE AND AMOUNT OF HUMAN INTERLEUKIN-3 IN A SAMPLE USING NOVEL IL-3 ANTIBODIES

(71) Applicant: UNIVERSITATSKLINIKUM REGENSBURG, Regensburg (DE)

(72) Inventors: Matthias Mack, Regensburg (DE); Hilke Brühl, Regensburg (DE); Kerstin Renner, Tegernheim (DE)

(73) Assignee: Universitätsklinikum Regensburg (DE)

( * ) Notice: Subject to any disclaimer, the term of this patent is extended or adjusted under 35 U.S.C. 154(b) by 0 days.

(21) Appl. No.: 15/626,812

(22) Filed: Jun. 19, 2017

(65) Prior Publication Data

US 2017/0291941 A1   Oct. 12, 2017

Related U.S. Application Data

(62) Division of application No. 14/400,958, filed as application No. PCT/EP2013/061122 on May 29, 2013, now Pat. No. 9,714,286.

(30) Foreign Application Priority Data

May 29, 2012  (EP) .................................... 12169805

(51) Int. Cl.
- *C07K 16/24* (2006.01)
- *G01N 33/68* (2006.01)
- *G01N 33/564* (2006.01)

(52) U.S. Cl.
CPC ......... *C07K 16/244* (2013.01); *G01N 33/564* (2013.01); *G01N 33/6869* (2013.01); *C07K 2317/33* (2013.01); *C07K 2317/92* (2013.01); *G01N 2333/5403* (2013.01); *G01N 2800/102* (2013.01)

(58) Field of Classification Search
None
See application file for complete search history.

(56) References Cited

U.S. PATENT DOCUMENTS

| | | |
|---|---|---|
| 9,714,286 B2 | 7/2017 | Mack et al. |
| 2015/0175693 A1 | 6/2015 | Mack et al. |
| 2015/0338420 A1 | 11/2015 | Mack et al. |
| 2016/0264660 A1 | 9/2016 | Mack et al. |

FOREIGN PATENT DOCUMENTS

| | | |
|---|---|---|
| EP | 2193790 A1 | 6/2010 |
| WO | 2005051999 A2 | 6/2005 |
| WO | 2010063488 A1 | 6/2010 |
| WO | 2010094068 A1 | 8/2010 |

OTHER PUBLICATIONS

U.S. Appl. No. 14/400,954, "Advisory Action", dated May 19, 2017, 4 pages.
U.S. Appl. No. 14/400,954, "Final Office Action", dated Jan. 25, 2017, (15 pages).
U.S. Appl. No. 14/400,954, "Non-Final Office Action", dated Jun. 16, 2016, (24 pages).
U.S. Appl. No. 14/400,954, "Notice of Allowance", dated Jun. 30, 2017, (11 pages).
U.S. Appl. No. 14/400,954, "Restriction Requirement", dated Jan. 13, 2016, (10 pages).
U.S. Appl. No. 14/400,958, "Non-Final Office Action", dated Sep. 8, 2016, (15 pages).
U.S. Appl. No. 14/400,958, "Notice of Allowance", dated Apr. 10, 2017, (7 pages).
U.S. Appl. No. 14/400,958, "Restriction Requirement", dated Feb. 29, 2016, (8 pages).
Abrams , "Immunoenzymetric assay of mouse and human cytokines using NIP-labeled anti-cytokine antibodies", Curr Protoc Immunol. Chapter 6:Unit 6.20, 1995.
Almagro , "Humanization of antibodies", Frontiers in Bioscience, Albertson, NY, US, vol. 13, Jan. 2008, pp. 1619-1633.
Anonymous, "Human IL-3 Antibody", http://www.mdsystems.com/pdf/mab603.pdf, Jan. 1, 2011.
Anonymous, "Human IL-3 Elisa Kit—User Manual", http://www.ravbiotech.com/manual/ELISAIELH-11.3-001.pdf, Mar. 1, 2012.
Anonymous, "Technical Data Sheet Biotin Rat Anti-human-IL-3", BD Biosciences, http://www.bdbi OSel en ces.comiextemal files/pm/dm/kis/ban/live/web enabled/20572D 554674.pdf, 2007.
Beerli et al., "Isolation of human monoclonal antibodies by mammalian cell display", PNAS, vol. 105, No. 38, pp. 14336-14341, 2008.
Brown et al., "Tolerance of single, but not multiple, amino acid replacements in antibody VH CDR 2: A means of minimizing B cell wastage from somatic hypermutation", The Journal of Immunology, vol. 156(9), pp. 3285-3291, May 1996.
Brühl et al., "Important role of interleukin-3 in the early phase of collagen-induced arthritis", Arthritis Rheum., vol. 60, No. 5, pp. 1352-1361, 2009.
Duronio et al., "Antibodies to interleukin 3 as probes for the interaction of interleukin 3 with its receptor", Cytokine, Academic Press Ltd., 3(5), pp. 414-420, 1991.
EP12169799.9, "Extended European Search Report", dated Nov. 9, 2012, 9 pages.
Hemminki et al., "Familial associations of rheumatoid arthritis with autoimmune diseases and related conditions", Arthritis & Rheumatism, 60(3), pp. 661-668, 2009.
Jakobovits et al., "From XenoMouse technology to panitumumab, the first fully human antibody product from transgenic mice", Nature Biotechnology, 25(10), pp. 1134-1143, 2007.

(Continued)

*Primary Examiner* — Vanessa L. Ford
*Assistant Examiner* — Jegatheesan Seharaseyon
(74) *Attorney, Agent, or Firm* — Kilpatrick Townsend & Stockton LLP

(57) ABSTRACT

For determining the presence and amount of human interleukin 3 (IL-3) in a sample, the present invention provides a diagnostic method, wherein an anti-IL-3-antibody, fragment or construct thereof is added to said sample under conditions which allow for binding said antibody, fragment or construct thereof to IL-3 and detecting the amount of antibody bound IL-3 in said sample, wherein the anti-IL-3-antibody is clone 13. Further subject matter of the present invention are the novel antibody clone 13, a nucleic acid encoding said antibody and a hybridoma cell line which produces antibody clone 13. A diagnostic assay kit contains all necessary reagents and materials for performing such assay, preferably an ELISA assay and especially preferably contains antibody clones 13 and 11.

3 Claims, 19 Drawing Sheets

(56) References Cited

OTHER PUBLICATIONS

Jeong et al., "Recombinant antibodies: engineering and production in yeast and bacterial hosts", Biotechnology Journal, vol. 6, pp. 16-27, 2011.

Jones et al., "Replacing the complementarity-determining regions in a human antibody with those from a mouse", Nature. vol. 321(6069), pp. 522-525, 1986.

Kaushansky et al., "Structure-function relationships of interleukin-3. An analysis based on the function and binding characteristics of a series of interspecies chimera of gibbon and murine interleukin-3", J Clin Invest., vol. 90, no. 5, pp. 1879-1888, 1992.

Knopf et al., "A time-resolved fluoroimmunoassay for recombinant human interleukin-3", Annals of Clinical Biochemistry, vol. 30, No. 1, pp. 69-71, 1993.

Kontermann et al., "Recombinant antibodies", Antibody Engineering, Laboratory Manuals, Springer Lab Manual, Chapter I, pp. 3-16, 2001.

Lantz et al., "Role for interleukin-3 in mast-cell and basophil development and in immunity to parasites", Nature, vol. 392, pp. 90-93, 1998.

Li et al., "A comparative study of different vector designs for the mammalian expression of recombinant IgG antibodies", Journal of Immunological Methods, vol. 318, pp. 113-124, 2007.

Lokker et al., "Structure-activity relationship study of human interleukin-3 role of the carboxyl-terminal region for . biological activity", EMBO Journal, vol. 10, No. 8, pp. 2125-2132, 1991.

Metcalf, "The hemopoietic colony stimulating factors", Elsevier Science Publishers B.V., pp. 54-91, 1984.

Padyukov et al., "A Gene-Environment Interaction Between Smoking and Shared Epitope Genes in HLA-DR Provides a High Risk of Seropositive Rheumatoid Arthritis", Arthritis & Rheumatism, vol. 50, No. 10, pp. 3085-3092, 2004.

Papoian et al., "A sensitive ELISA for measuring recombinant human interleukin-3 in human plasma or serum", J Immunol Methods, vol. 145, No. 1-2, pp. 161-165, 1991.

PCT/EP2013/061121, "International Preliminary Report on Patentability", dated Dec. 11, 2014, 9 pages.

PCT/EP2013/061121, "International Search Report and Written Opinion", dated Aug. 13, 2013, 11 pages.

PCT/EP2013/061122, "International Preliminary Report on Patentability", dated Dec. 11, 2014, 9 pages.

PCT/EP2013/061122, "International Search Report and Written Opinion", dated Jul. 11, 2013, 13 pages.

Presta, "Molecular engineering and design of therapeutic antibodies", Current Opinion in Immunology, vol. 20, pp. 460-470, 2008.

R&D Systems, "Human IL-3 polyclonal goat IgG AF-203-NA", http://www.mdsystems.comipfdiaf203na.pdf, 2011.

Santos et al., "Development of more efficacious antibodies for medical therapy and diagnosis", Progress in Nucleic Acid Research and Molecular Biology, vol. 60, pp. 169-194, 1998.

Vajdos et al., "Comprehensive functional maps of the antigen-binding site of an anti-erbB2 antibody obtained with shotgun scanning mutagenesis", J Mol Biol. vol. 320(2), pp. 415-428, 2002.

Fig. 1

Aminoacid identity of IL-3 between various species

- Human - Mouse: 29%
- Human - Rat: 30%
- Mouse - Rat: 60%
- Human – Marmoset: 72%
- Human - Rhesus: 84%
- Human - Chimpanzee: 99%

Human IL-3 is partially active in Rhesus but not in Marmoset
Rhesus IL-3 is active in humans Fig. 9
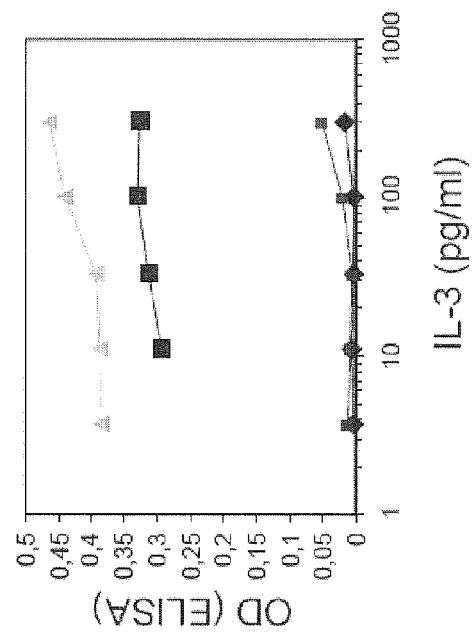
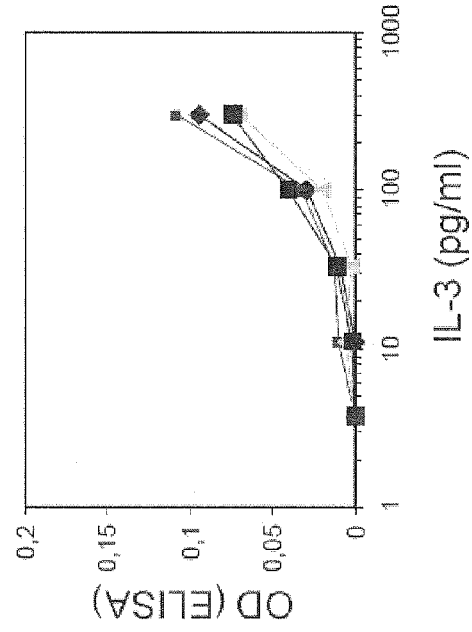

Development of a diagnostic IL-3 ELISA

Dilution of IL-3 in PBS+1% BSA

DIAGNOSTIC METHOD FOR DETERMINING THE PRESENCE AND AMOUNT OF HUMAN INTERLEUKIN-3 IN A SAMPLE USING NOVEL IL-3 ANTIBODIES

CROSS REFERENCE TO RELATED APPLICATIONS

The present application is a divisional application of U.S. patent application Ser. No. 14/400,958, filed Nov. 13, 2014, which is the National Stage Application under 35 U.S.C. § 371 of International Application No. PCT/EP2013/061122, filed May 29, 2013, which claims priority to European Patent Application No. 12169805.4, filed May 29, 2012, all of which are hereby incorporated herein by reference in their entireties.

The present invention relates to diagnostic methods for reliably determining the presence and the amount of human interleukin-3 (hIL-3) in a sample, preferably in the blood, plasma, serum or any other body fluid (e.g. urine, synovial fluid) of a human patient. The invention further relates to novel anti-IL-3 antibodies used in the diagnostic method, nucleic acid sequences encoding and hybridoma cell lines producing the antibodies according to the present invention and test kits providing the essential reagents for the diagnostic method.

Interleukins belong to the large family of proteins called cytokines. Cytokines are polypeptides that influence the function of certain cells upon binding to specific cellular receptors and are divided in subclasses, i.e., interleukins, interferons, colony-stimulating factors (CSFs), lymphokines, growth factors and monokines. It is well known that cytokines play a major role in cell proliferation and, e.g., also inflammatory diseases.

Cell proliferation is a complex process wherein growth factors bind to specific receptors on the cell surface, whereupon endocytosis occurs and the complexes of cytokine and receptor are internalized causing a cellular response. Such cellular responses include specific gene transcription activities as DNA synthesis and cell replication. When tested in relatively high concentrations, most of the cytokines have several differing biological effects. Because of these effects of cytokines, there is a high interest in investigations for possible therapeutic uses of these proteins.

Interleukins are mediators of the immune system which are produced in low concentration mostly in leukocytes. They influence the growth, differentiation and activity of cells of the immune system and thus belong to the immune modulators. They also take effect by binding to receptors on the surface of target cells and thus change the transcription rate of certain genes. They play an important role in the triggering of a multiplicity of cellular responses.

Interleukins are, e.g., involved in the immunological cell activation cascade and subsequent inflammatory changes. Irregular and/or abnormal inflammation is a major component and factor of a wide range of human diseases, one of which is the immunological disorder rheumatoid arthritis (RA). But also other immunological diseases are influenced by interleukins.

IL-3, also designated as Multi-CSF, is a well-known member of the interleukin family. It has a growth stimulating and differentiating effect on various hematopoietic precursor cells and acts as a growth factor for mast cells. Together with IL-5 and GM-CSF, IL-3 belongs to the family of hematopoietic cytokines with four short alpha-helical bundles. GM-CSF and IL-3 stimulate the formation of neutrophilic and eosinophilic granulocyte colonies as well as macrophages. It further stimulates the formation of mast, megakaryocyte and pure and mixed erythroid colonies (D. Metcalf, "The hematopoietic colony-stimulating factors", 1984, Elsevier, Amsterdam).

IL-3 consists of 133 amino acids and is known for its stimulation of colony formation by human hematopoietic progenitor cells and the stimulation of DNA synthesis by human acute myelogenous leukemia (AML) blasts. IL-3 binds to a unique receptor also known as CD123 antigen. The receptor belongs to the type I cytokine receptor family and is a heterodimer with a unique α-chain paired with a common β-subunit (βC or CDW 131). IL-3 binds to the unique α-receptor subunit. Signal transduction is mediated, however, by the common β-receptor subunit (βC) by the JAK2-STAT5 pathway.

IL-3 is mainly produced by activated CD4+ T-cells and contributes especially to growth, differentiation and survival of CD34+ hematopoietic progenitor cells. In vitro, IL-3 has been observed to promote the differentiation of basophiles and mast cells from bone marrow cells. It has further been observed to induce IL-6 release by murine basophils and to up-regulate MHC-II expression and IL-1 secretion in monocyte/macrophages. Further, IL-3 supports the differentiation of monocytes into dendritic cells and osteoclasts.

Since the first detection of IL-3 in a human genomic library, it has been a focus of investigations to determine its role in healthy humans as well as its possible role in the occurrence of diseases. The ability of cytokines to initiate or regulate hematopoieses is of interest, especially as far as malfunctions or diseases of the immune system are concerned. Such disorders seem to be connected to disturbances of the hematopoietic system and it was assumed that such diseases could be treated by providing viable progenitor cells to the hematopoietic system. Triggering such progenitor cells to differentiate was considered as a means to treat the respective diseases.

Until several years ago, little was known about the role of IL-3 in autoimmune diseases and especially rheumatoid arthritis (RA). RA is the most prevalent inflammatory disease of the joints. The initial disease stages often develop gradually but can also manifest themselves with an instantaneous outburst. While pain occurs predominantly in joints of the fingers or toes, also other joints can be affected. The affected joints show swelling and usually are hyperthermic. Mostly, the disease proceeds in episodes, an episode usually lasting between several weeks to months. In between episodes, generally, there is an improvement of symptoms.

The etiology of RA is not yet known. An autoimmune cause is strongly suspected with viral and bacterial causes being also discussed. A genetic influence has been reported by several authors (Hemminki K. et al., Arthritis Rheum. 2009; 60(3): 661-8, Padyukov L. et al., Arthritis Rheum. 2004; 50(10) 3085-92). It is assumed that misdirected immune cells invade the affected joints and cause the production of pro-inflammatory cytokines. According to one theory, the balance between cytokines is disturbed in RA. It has been reported that IL-1, IL-6 and TNFα are present in excess in RA and are assumed to be responsible for the deleterious inflammatory processes in cartilage tissue and for the activation of osteoclasts.

The treatment of rheumatoid arthritis is still considered difficult and burdensome to the patients since medications with a high risk of adverse side effects have to be used. One way of treating the disease is to perform a symptomatic treatment, mostly using non-steroidal anti-inflammatory drugs (NSAIDs). These drugs act as anti-inflammatory and analgetic agents and often only achieve an alleviation of pain. The drugs further interfere with a certain step in the inflammatory cascade, where prostaglandine is generated by cyclooxygenases. NSAIDs, however, do not influence the underlying inflammatory process and are thus not able to retard the joint destruction, which is the most deleterious effect of RA.

To prevent joint destruction and disease activity, a further current approach for treating RA is the use of disease-modifying anti-rheumatic drugs (DMARDs). These pharmaceuticals actually modify the disease process. Examples of DMARDs are methotrexate, the most commonly used anti-rheumatic, the effect of which is based on a reversible inhibition of the enzyme dihydrofolate reductase. Another commonly used substance for treating RA is leflunomide, which provides an effect by intervening with the pyrimidine metabolism. Both pharmaceuticals are long-acting and thus have to be administered over a longer period of time (usually 12-16 weeks) to show the desired effects. To bridge the time until DMARDs improve the disease, most patients are administered steroids.

A further approach for treating RA are "biologicals" that block cytokines like TNF, IL-6, IL-1 or costimulatory molecules like B7 or that deplete leukocyte subsets (e.g. B cells). Biologicals (e.g. the TNF antibody Infliximab) are mostly used for severe disease processes and after DMARDs have failed to sufficiently control disease activity. Biologicals influence a plurality of signal systems in the immune system and have a variety of serious side effects including bacterial and viral infections and a higher risk for development of neoplasia.

All known treatments have severe disadvantages and side effects and, therefore, it was desirable to develop new drugs for the treatment of RA which are effective but have less side effects than the currently used treatment regimes.

More recently, an involvement of IL-3 in autoimmune diseases and especially in RA has been described. WO 2010/063488 describes that IL-3 inhibitors can be used in treatment of early stages of rheumatoid arthritis. Although the patent application mentions that no IL-3 mRNA was detected in the synovium of patients with RA and no effect of IL-3 was observed on cultured fibroblasts, a genetic analysis found an association between a single nucleotide polymorphism in the IL-3 promoter gene and RA. Based on this finding and also further studies which show the presence of considerably elevated levels of IL-3 in RA patients, WO 2010/063488 proposes such use of inhibitors, mainly antibodies or antibody fragments, antibody variants or antibody multimers in prophylactic RA treatment, therapeutic treatment in early stages of the disease or in maintenance treatment.

However, there is still a need for effective antibodies with high specificity towards IL-3 which also show a high affinity and avidity. Such antibodies are desirable for an envisioned therapeutic use but also for a meaningful and reliable diagnosis. Test results that have been produced within the research framework that led to the present invention indicate that not in all RA patients symptoms and systemic inflammation correlate with an elevated IL-3 level. Obviously there are different groups of RA patients as far as involvement of IL-3 in the propagation of the disease is concerned. Accordingly, patients that do not show elevated levels of IL-3 in acute phases of the disease, most probably would not benefit from a treatment with anti-IL-3 antibodies. Unprofitable expenses to the health system can be avoided by a reliable diagnostic test with regard to the presence of IL-3 in the blood or serum of patients.

Apart from the outlined relevance of IL-3 in RA, another advantageous implementation of the determination of elevated levels of IL-3 could be seen in the field of coronary artery and heart diseases. Elevated levels of IL-3 have e.g. been considered relevant for the prediction of restenosis after coronary intervention (Rudolph, T. et al. (2009) Int. J. Cardiol. 132:392). Further elucidation of the role of IL-3 might suggest other conditions in which IL-3 levels have medical relevance and therefore need to be monitored.

Currently available commercial diagnostic test kits for IL-3 determination have not proven sufficiently reliable when conducted directly on blood, plasma or serum. Therefore, it was the object of the present invention to provide diagnostic methods and test kits for use in such methods which allow for a very specific and reliable detection and quantification of IL-3.

This object was solved according to a first embodiment of the invention by a diagnostic method for determining the IL-3 level in a sample which preferably is a body fluid and more preferably is blood, plasma or serum of a patient. The method according to the present invention comprises adding an anti-IL-3 antibody, antibody fragment or antibody construct to said sample under conditions which allow for binding of said antibody, fragment or construct thereof to IL-3 and detecting the amount of antibody-bound IL-3 in said sample, wherein the anti-IL-3 antibody is clone 13 (DSM ACC3164).

For a reliable qualitative and quantitative determination of IL-3 in a body fluid sample, it is especially important that the antibodies used in such method show little or no cross-reactivity with other cytokines and interleukins like IL-5 an GM-CSF which are often also present in substantial amounts in body fluids of patients.

Antibody clone 13 is a mouse anti-human IL-3 antibody which shows a high specificity and affinity for IL-3. It is considered to bind to a 3D epitope of IL-3 in its native conformation. According to the present invention, antibody clone 13 and optionally further antibodies having similar characteristics are used for the detection of the presence and/or amount of IL-3 in any suitable immunoassay format.

Apart from a very high specificity for only IL-3 but not other cytokines, antibody clone 13 also shows very low levels of cross-reactivity with IL-3 molecules of other mammalian origin. Although amino acid identities for the human protein and the mouse protein is only 29%, for marmoset, rhesus or a chimpanzee proteins there are amino acid identities between 72 and 99% (FIG. 1). Nevertheless, it could be shown that for clone 13 there was no detectable cross-reactivity with IL-3 from mouse, rat or rhesus. From the further cytokines, which may also be present at an elevated level in autoimmune diseases, IL-5 and GM-CSF are particularly important. A high cross-reactivity of an anti-IL-3 antibody with such cytokines in an immunoassay can lead to incorrect results regarding the fact whether an IL-3 overexpression has an important influence in the manifestation and progression of the autoimmune disease. Such results, however, have an important impact e.g. on the decision whether the application of an anti-IL-3 antibody can be considered a promising therapeutic approach.

It is thus preferred for antibodies used in the diagnostic method of this invention to show the lowest possible cross-reactivity with human IL-5 and GM-CSF. Particularly preferred, it is a characterizing feature of such an antibody that it binds to IL-5 or GM-CSF to an extent of below 5%, more preferred below 2% and particularly preferred below 1% as compared to the amount of IL-3 bound by the antibody.

The examples enclosed with this specification show the superior characteristics with regard to specificity and lack of cross-reactivity with IL-3 of other species and with other human cytokines for antibodies used according to the present invention. In experiments which are detailed in the Examples enclosed to the present specification, clone 13 has been proven to be useful for ELISA immunoassays using blood, plasma or serum as samples and which show a very high sensitivity as well as specificity towards hIL-3 and enable the detection of levels of IL-3 already in the pg/ml range. Further, such diagnostic tests using clone 13 reliably detect IL-3 even in samples that have been stored at room temperature, in the refrigerator or the freezer.

In a preferred embodiment of the present invention, the diagnostic method is conducted as an ELISA assay. The general test regime used for ELISA assays is well known to the skilled person. At least two antibodies which bind to the target molecule are used. One of these antibodies is bound to a solid phase allowing for the separation of the antigen to be determined from the test sample. Upon removal of the test sample from the solid phase and washing steps as considered appropriate, a second antigen-specific and labeled antibody is added and after further removal of excess labeled antibody and optionally further washing steps the amount of label bound via the antibody-antigen-antibody complex is determined and correlated to the amount of antigen present.

Although it is necessary that both antibodies used in such an ELISA assay are specific to the antigen to a high extent, an especially high degree of specificity is needed in at least one of the two antibodies involved. E.g., as a first solid phase-bound antibody a very specific antibody can be used to be able to separate only the desired antigen from the liquid sample without any cross-reacting background. If only the desired antigen is coupled via the antibody to the solid surface, the specificity of the second antibody is not so decisive anymore since unspecific binding to other antigens is not an issue in such a case. Accordingly, it is possible to use a less specific antibody as the second antibody in such a context.

Alternatively, it is possible to use a high affinity and high avidity antibody as the first solid phase-bound antibody and to use a highly specific antibody as the second and labeled antibody. In such an embodiment, unspecific binding of other antigens like IL-5 or GM-CSF might take place to some extent due to a certain cross-reactivity of the first antibody, however, the actual detection by the labeled antibody is then restricted to IL-3 by using a highly specific second antibody.

Of course, best results are obtained when two highly specific anti-IL-3 antibodies are used in such a method which is then also an especially preferred embodiment of the present invention.

To avoid possible steric hindrance issues for the ELISA performance, it is preferable to use a second antibody that binds to an epitope of IL-3 at another part of the protein as antibody clone 13. It is well within the ambit of the present invention to use a known and commercially available antibody as the second antibody. However, according to the present invention, preferred combinations of antibodies (first solid-phase bound antibody/second labeled antibody) are clone 13/11 (most preferred), clone 11/13 (preferred), clone 13/44, clone 44/13, clone 14/47, clone 47/13 as well as combinations of clones 11 or 44 with clone 47. The above mentioned clones were deposited at DSMZ in Braunschweig/Germany: clone 11 (11.14.6)=DSM ACC3163; Clone 13 (13.4.4)=DSM ACC3164; Clone 44 (44.16.16)=DSM ACC3166; clone 47 (47.28.15)=DSM ACC3167.

The antibodies used in the diagnostic method according to the present invention can be of different nature and the following more detailed illustrations of possible antibodies or antibody constructs are only meant to be exemplary. That means that within the context of the present invention the term antibody is to be understood in its broadest sense. Any antibody, part thereof or construct containing antibody characteristics and retaining the specificity of the antibodies shown in the examples of the present invention, is considered as encompassed within the term antibody in the context of the present invention.

In principle, monoclonal antibodies as well as polyclonal antibodies can be used. Monoclonal antibodies generally have the advantage of a higher specificity as compared to polyclonal antibodies and are thus preferred in view of the present invention. In terms of the present invention, the term "antibody" shall also comprise fragments, bi-, tri- or multimeric or bi-, tri- or multifunctional antibodies having several antigen binding sites which preferably are IL-3-specific binding sites. Regarding the present invention, the term "antibody" further comprises fusion proteins containing as a part of the fusion protein an antibody or antibody fragment or complement determining region (CDRs) of an antibody of the present invention, which show a corresponding specificity and which have furthermore retained their binding ability to IL-3. Further comprised are single chain antibodies. Moreover, the inventive antibodies can belong to any appropriate antibody class, it is however essential that their use in therapy and diagnostics is possible. Preferably, the anti-IL-3 antibody or the fragment thereof according to the present invention is of the class IgG, IgA, IgE oder IgM.

In summary, for the purpose of the present invention, the actual form of a molecule considered to be encompassed by the term "antibody" is irrelevant as long as it specifically binds to IL-3 in diagnostic assays.

Accordingly, also antibody fragments or constructs as outlined above which are derived from antibody clone 13 as well as clone 11, clone 44 and clone 47 can be used in the method of the invention. The specific anti-IL-3 antibodies used according to the present invention can be produced by any method known to the skilled person. For example, antibodies can be generated using the complete hIL-3 protein as an immunogen and lateron selecting for antibodies and antibody clones which are specific for the mentioned sequences. As an alternative, a peptide containing within its sequence the desired parts or epitopes of IL-3 can be used for immunization. A further possibility is the use of artificial epitopes which contain only the very epitope (conformationally discriminating epitope, CDE) integrated into an environment which allows for the generation of antibodies. Such methods are known to the skilled person and described e.g. in WO2005/051999. In summary, any method for producing antibodies is useful within the context of the present invention as long as it produced antibodies with the required specificity and if necessary allows for the selection of suitable antibodies from a plurality of antibodies which are produced upon immunization with IL-3 or parts thereof.

Such anti-IL-3-antibody can also be of any origin, e.g. human, mouse, goat, rabbit. As a commonly used method, the production of antibodies is carried out by immunizing appropriate mammals, e.g., mice, rat, hamster or rabbits.

By means of an enzyme-linked immunosorbent assay (ELISA), the specifity and cross-reactivity of the produced antibodies can be easily determined. In this context, recombinantly produced cytokines (e.g. human IL-3, IL-5 and GM-CSF, or IL-3 from other species, respectively) are coated onto a suitable surface in the test arrangement, the produced anti-human-IL-3-antibodies are added and their binding is detected on the coated surface by means of a corresponding detection reagent, such as a labelled anti-IgG-antibody. In such a test regimen, antibodies according to the present invention bind nearly exclusively to IL-3 while binding to IL-5 and GM-CSF occurs only to a very minor extent, if at all. The same is true for the antibodies as far as IL-3 from other species is concerned.

For the selection of particularly suitable antibodies, the affinity of same is examined by further ELISA assaying. In this context, ELISA plates are coated with any anti-human-IL-3 antibody which can also be a commercially available antibody (e.g., a goat IgG anti-human-IL-3 antibody). In this respect, for instance, 1 ug/ml of the antibody is incubated with the ELISA plates over night in a refrigerator whereupon a washing step, a blocking step and incubation with human IL-3 (250 ng/ml in PBS buffer) is performed, thus fixing human IL-3 on the solid phase. During such a test, candidate antibodies are then added in different concentrations and detected by means of a secondary HRP- (horseradish peroxidase) labelled polyclonal antibody.

A particularly preferred antibody which according to the present invention is used in an ELISA assay as a second or further antibody together with antibody clone 13 is clone 11. Clone 11 is a mouse anti-human-IL-3 antibody and shows a very high specificity and affinity to IL-3. Clone 11 specifically binds to the epitope with the amino acids SWVN according to SEQ ID NO: 2. This particularly preferred antibody was deposited at DSMZ (Braunschweig, Germany) under number DSM ACC3163.

In many experiments and also in the examples enclosed to the present specification, clone 11 has proven very superior characteristics with regard to specificity, lack of cross-reactivity but also with regard to affinity and avidity. This preferred antibody therefore is considered especially suitable for use in diagnostics as well as therapeutic measures.

A further especially preferred antibody used in an ELISA assay according to the present invention is clone 44 which has been deposited at DSMZ under the accession number DSM ACC3166. Clone 44 is considered to bind specifically to the same epitope as clone 11.

A further especially preferred antibody used in an ELISA assay according to the present invention is clone 47 which has been deposited at DSMZ under the accession number DSM ACC3167. Clone 47 is considered to bind to a three dimensional (3D) epitope.

A second embodiment of the present invention is novel antibody clone 13.

A further subject-matter and third embodiment of the present invention is a nucleic acid which encodes antibody clone 13 or an antibody fragment, an antibody construct or sequences for CDRs conveying specificity of antibody clone 13 according to the present invention. Besides the production of antibodies via the immunization of animals/mammals route and/or via the hybridoma technique for the production of monoclonal antibodies, it has for some time now also been established to produce antibodies by means of recombinant methods.

Hence, it is also possible to use respective nucleic acids to produce e.g. antibody fragments in bacteria or eukaryotic cells. Corresponding methods for producing recombinant antibodies or antibody fragments are known to a person skilled in the art (see e.g., Jeong K J, Jang S H, Velmurugan N., Biotechnol J. 2011 January; 6(1):16-27. Recombinant antibodies: engineering and production in yeast and bacterial hosts; Li J, Menzel C, Meier D, Zhang C, Dübel S, Jostock T., J Immunol Methods. 2007 Jan. 10; 318(1-2):113-24. A comparative study of different vector designs for the mammalian expression of recombinant IgG antibodies).

A further subject-matter and embodiment of the present invention is the hybridoma cell line which produces antibody clone 13, the cell line designated 13.4.4 (DSM ACC3164).

A further and final embodiment of the present invention is a test kit to be used in the diagnostic method according to the present invention. Such a test kit contains as an essential element antibody clone 13 as well as other materials and reagents necessary and useful for the immunoassay for detection of IL-3. Clone 13 and other useful as well as preferred antibodies for the immunoassay and especially ELISA assay are described above. Further materials necessary for the assays as well as useful buffers, labels and other reagents e.g. for determining the amount of label which is indicative of the amount of IL-3 present in the sample are known to the skilled person. Such test kits can be provided for easy and effective use in laboratories of every size. Test kits according to the present invention contain in an especially preferred embodiment of the present invention a combination of antibody clones 13 and 11, wherein both antibodies can be provided either as solid phase bound antibody or as the antibody carrying the detectable label.

As already mentioned above, it has been noted that presently available antibodies and test kits for detecting and measuring IL-3 in a sample do not deliver accurate enough results to base a therapeutic approach thereon. Especially for whole blood, plasma and serum, results of commercially available test kits have proven to be unreliable because of high background levels and unspecific cross-reaction being indistinguishable from actual IL-3 binding. Also the binding affinity of known antibodies to IL-3 present in samples of patient blood, plasma or serum has proven insufficient for a correct analysis of a possible influence of IL-3 in an autoimmune disease, especially in RA.

By using the clone 13 and other specific anti-IL-3 antibodies in diagnostic methods and corresponding test kits, the accurate determination of the presence of IL-3 in body fluids can be improved to a major extent and such methods and test kits, therefore, are a further subject matter of the present invention. It has surprisingly been found that using the antibodies and methods of the present invention, IL-3 could be specifically detected even if present in only picogram/ml concentrations in a sample. The relative affinity of the antibodies of the present invention towards IL-3 is thus about at least a factor 100 higher than the affinity of known antibodies.

Although it might be useful for diagnostic purposes to be able to detect IL-3 in any body fluid or also cell preparation, the present diagnostic method is especially suited and useful for the detection of IL-3 in a plasma or serum sample. With the heretofore known methods and antibodies, detection of IL-3 in plasma or serum did not lead to sufficiently meaningful results especially due to cross-reactivities of known antibodies and insufficient affinities of such antibodies with regard to the low levels of IL-3 in present blood, plasma or serum in healthy and in RA patients. Therefore, often synovial fluids were used as test sample. However, obtaining such a test sample is much more difficult and cumbersome to the patient. Use of the antibodies according to the present invention surprisingly opens up the possibility to reliably detect and draw conclusions from the presence of IL-3 in blood, plasma and serum. Thus, the present invention via its antibodies and their use in diagnosis is a big step forward to relating IL-3 presence to the severity of RA and RA incidents in patients and thus to also determine the supposition of a patient to treatment with IL-3 antibodies.

The following examples and figures further illustrate and describe the present invention but are not intended to limit the scope thereof.

FIG. 1 shows the amino acid sequence homology of IL-3 of various species;

FIG. 7 to 10 show the results of ELISA assays which were performed using differing combinations of coating and detection antibodies selected from the antibody clones 8, 11, 13, 44 and 47 as well as using a commercially available test kit. The results indicate that best performance can be achieved by using a combination of clones 13 and 11 and that these tests work tremendously well to detect and quantitate IL-3, even when body fluids (plasma, serum) are used as test samples.

FIG. 11 to 14 show the results of ELISA assays performed to investigate the stability of tests performed inter alia with plasma and serum and using as the coating (solid-phase bound) antibody clone 13 and as detection antibody HRP-labelled clone 11. Plasma and serum samples containing IL-3 were stored for the given periods of time at various temperatures. The test results confirmed very good stability and performance for the test formats.

Figure 15:
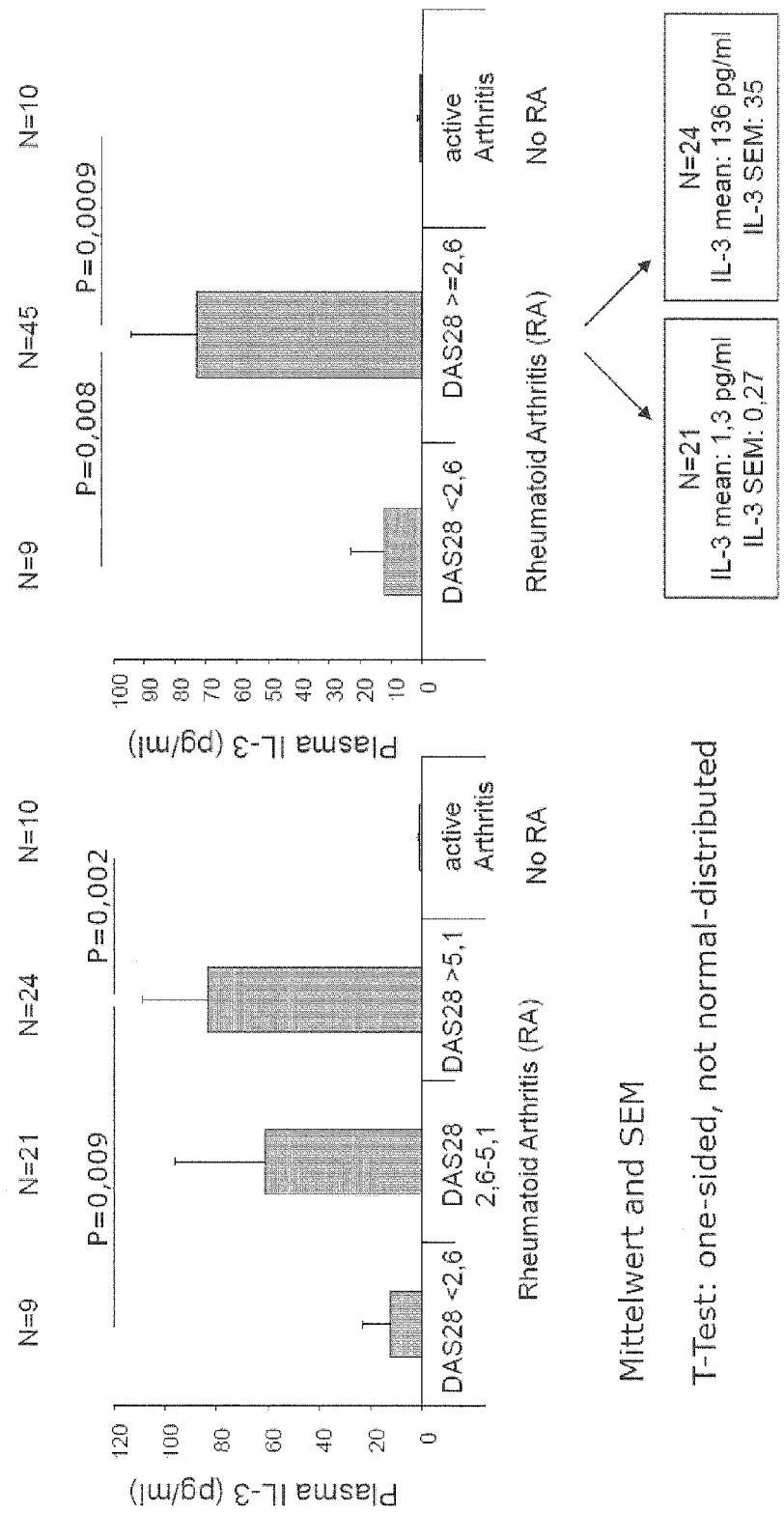
Figure 16:
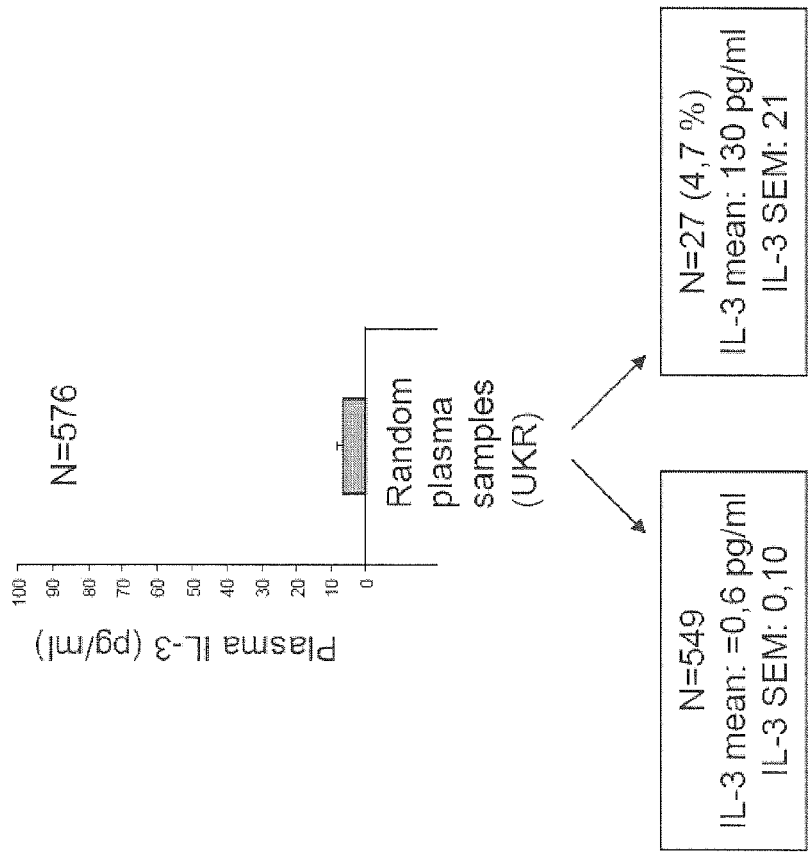

FIGS. 15 and 16 show clinical data regarding the plasma IL-3 levels of patients with or without active RA, as well as data showing an analysis of plasma IL-3 levels of randomly picked patients presenting at the University Hospital Regensburg. The results indicate that in general only a small percentage of randomly picked patients show IL-3 levels above 20 pg/ml, while more than 50% of patients with active RA have IL-3 levels above 20 pg/ml. Among confirmed active RA patients, there are two subgroups only one of which shows high plasma levels of IL-3.

Figure 17:
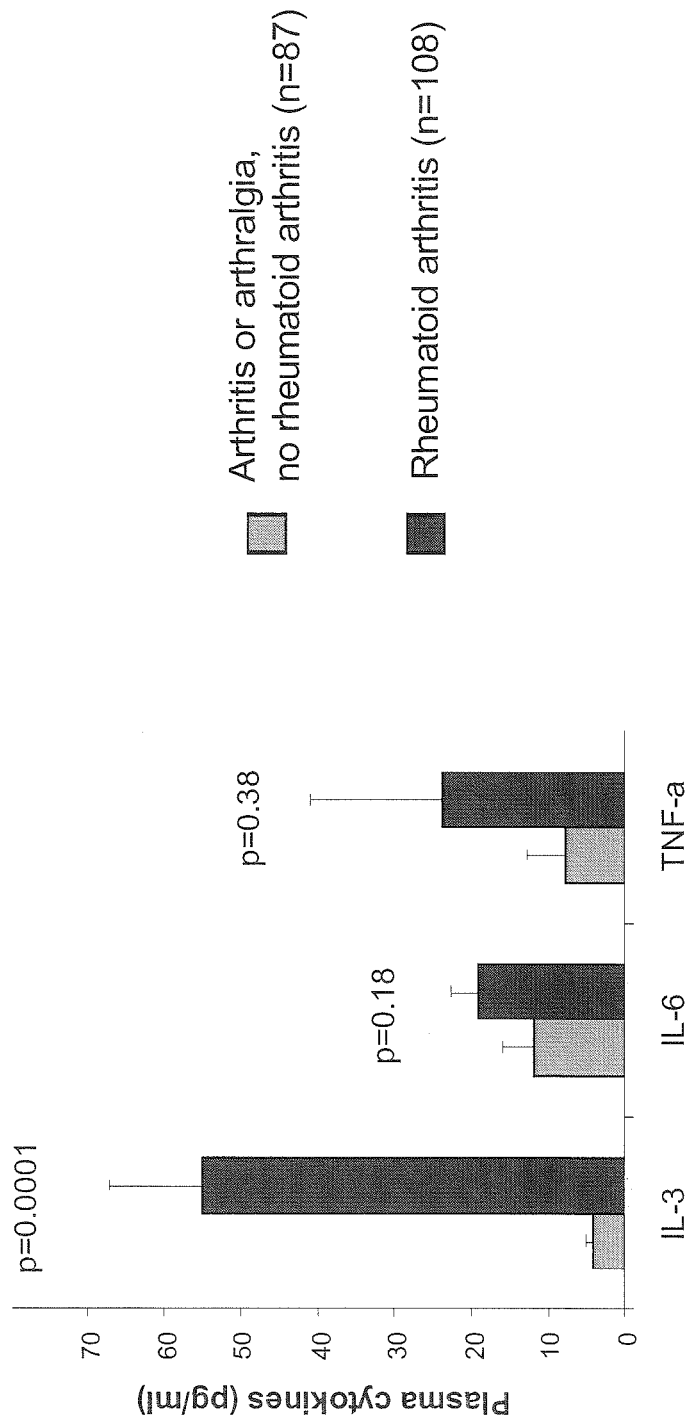
Figure 18:
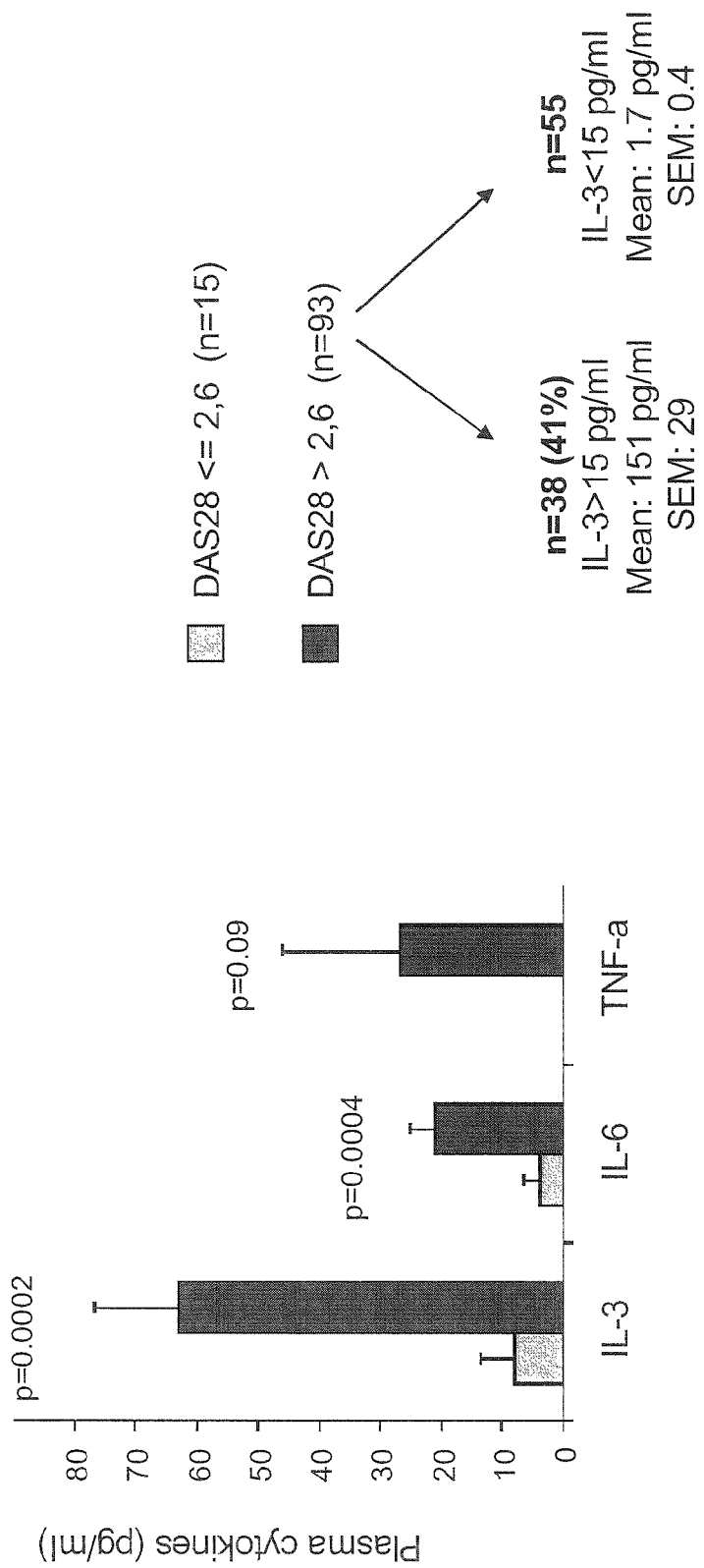

FIGS. 17 and 18 show clinical data regarding the plasma IL-3, IL-6 and TNF-α levels of patients with or without active RA (FIG. 17), as well as data showing an analysis of cytokine levels in patients with diagnosed RA (FIG. 18). The results indicate that IL-3 but not IL-6 or TNF-α can separate between RA and non-RA types of arthritis (FIG. 17). Furthermore, what can be concluded from the data presented in FIG. 18 is that IL-3 and IL-6 but not TNF-α correlate with disease activity in patients with RA.

Figure 19:
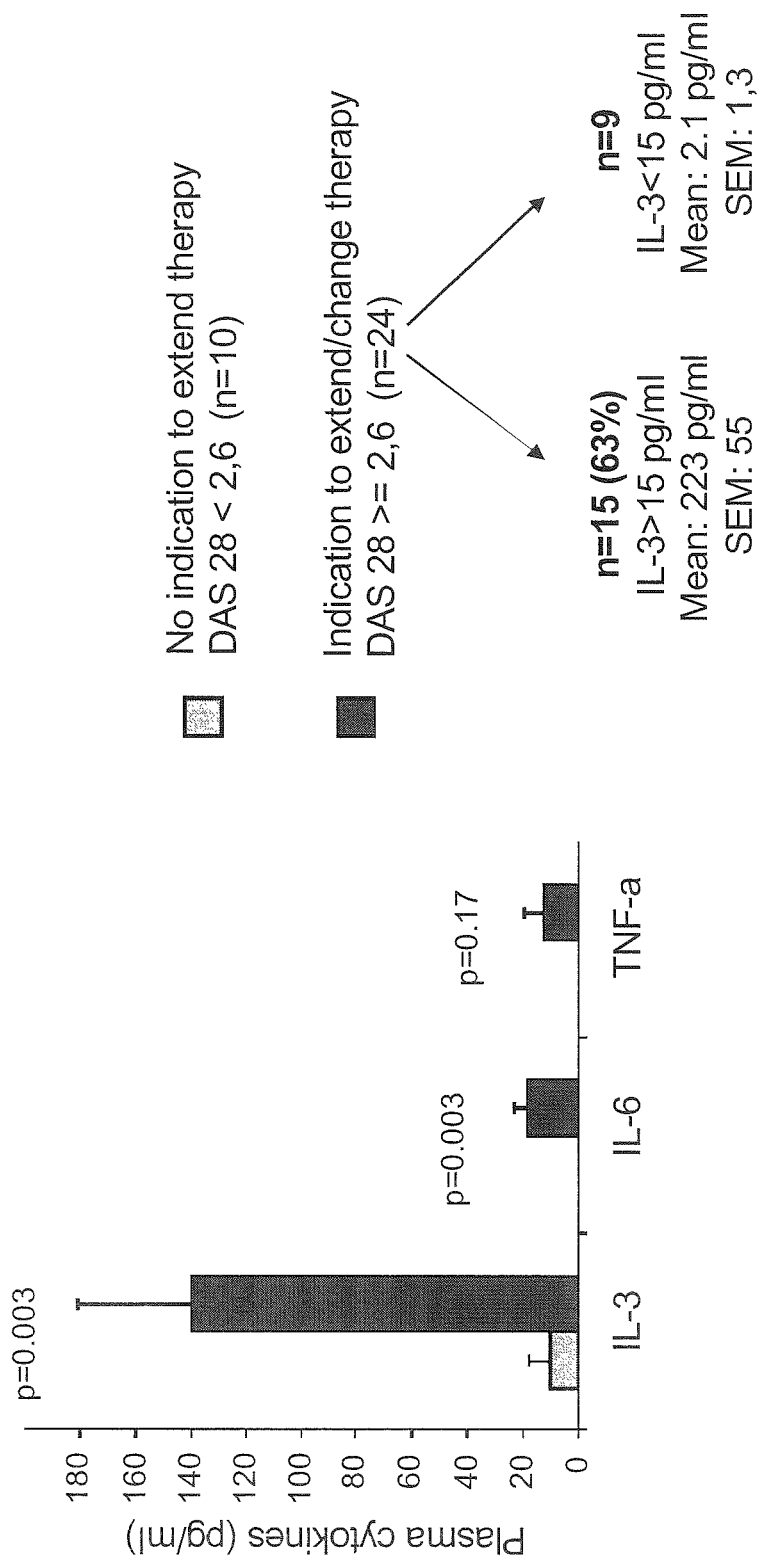

FIG. 19 shows clinical data regarding the plasma IL-3, IL-6 and TNF-α levels of RA-patients treated with DMARD and/or biologicals. The data indicate that 63% of RA patients not responding to DMARDs/biologicals express high IL-3 levels. Patients with high IL-3 levels are more frequent among those patients that did not respond to current therapies. These patients would qualify for treatment with anti-IL-3-antibodies.

EXAMPLE 1

Generation of Monoclonal Anti-IL-3 Antibodies

Anti-IL-3 antibodies were produced by immunizing Balb/c mice using at least 6 i.p. injections of human eukaryotic glycosylated IL-3 in alumn at four week intervals. Two days before cell fusion, IL-3 in PBS was injected intraperitoneally. Antibody-producing splenocytes obtained from the immunized mice (HGPRT positive, able to grow on HAT medium) were fused with the myeloma cell line X63Ag8.6.5.3 in the presence of polyethylene glycol (PEG) and a selection of hybridomas performed in an HAT-selection medium. Hybridomas were cultivated in RPMI-1640 medium supplemented by 10% FCS (neat inactivated, HIA), P/S and glutamine (1:100). Obtained cells are able to grow in suspension and are splitted every three days in a ratio of 1:4.

For storage purposes hybridoma cells are transferred from a cell culture bottle into 50 ml or 15 ml cell culture flasks (BD Falcon™). After centrifugation at 1400 rpm for 5 minutes at room temperature, the supernatant is completely removed. Cells are resuspended in a freezing medium (90% FCS (HIA)+10% DMSO) and 1.5 ml aliquots are filled into vials. The cells are prefrozen in a freezing container in a freezer at −80° C. and after 1-2 days transferred to a liquid nitrogen storage tank.

Cloning and recloning of the obtained hybridoma cell lines are performed using limited dilution to provide long-term stable sources for monoclonal antibodies.

Obtained antibodies are shown in table 1.

For determining the isotypes of the antibodies, ELISA assays were performed using hIL-3 coated plates to which the antibodies were added. Bound antibodies were detected using isotype specific secondary antibodies. For further analyses, only antibodies of isotype IgG were used.

TABLE 1

Overview of mAbs against human IL-3

| Original clone | First cloning | Second cloning | Isotype |
|---|---|---|---|
| Clone 2 | 2.28 | 2.28.11 | IgM, kappa |
| Clone 3 | 3.47 | 3.47.20 | IgG1, kappa |
| Clone 5 | 5.3 | 5.3.2 | IgM, kappa |
| Clone 6 | 6.38 | 6.38.14 | IgG1, kappa |
| Clone 7 | 7.42 | 7.42.45 | IgM, kappa |
| Clone 8 | 8.36 | 8.36.38 | IgG1, kappa |
| Clone 10 | 10.12 | 10.12.4 | IgG1, kappa |
| Clone 11 | 11.14 | 11.14.6 | IgG1, kappa |
| Clone 13 | 13.47 | 13.4.4 | IgG1, kappa |
| Clone 36 | 36.26 | 36.26.10 | IgG1, kappa |
| Clone 38 | 38.18 | 38.18.5 | IgG1, lambda |
| Clone 41 | 41.28 | 41.28.4 | IgG1, kappa |
| Clone 42 | 42.47 | 42.47.36 | IgG1, kappa |
| Clone 43 | 43.14 | 43.14.28 | IgG1, kappa |
| Clone 44 | 44.16 | 44.16.16 | IgG1, kappa |
| Clone 45 | 45.14 | 45.14.27 | IgG1, kappa |
| Clone 46 | 46.21 | 46.21.1 | IgG1, kappa |
| Clone 47 | 47.28 | 47.28.15 | IgG1, kappa |

EXAMPLE 2

Determination of the Amount of IgG1 in the Hybridoma Supernatants

Several of the obtained antibodies of the type IgG1 were isolated from hybridoma clones and their concentration determined. The determination of the concentration was performed according to following method: 96-wellplates are coated overnight at room temperature with anti-mouse IgG (1:100 in PBS) in a concentration of 100 µl/well. Blocking is performed by adding 100 µl per well of 2% BSA in PBS and incubation at room temperature for two hours. After the blocking reaction, the plates are washed twice. Two samples and blanks, respectively, of supernatants of clones 3.47.20, 6.38.14, 8.36.38, 10.12.4, 11.14.6 are incubated undiluted, as well as with dilutions of 1:3, 1:9, 1:27, 1:81, 1:243, 1:729 and 1:2187 (100 µl per well, dilution in 2% BSA in PBS) at room temperature. Mouse IgG1 in a starting concentration of 1 mg/ml is used as standard, whereas a concentration of 20 ng/ml is applied in dilutions of 1:2, 1:4, 1:8, 1:16, 1:32, 1:64 and 1:128.

The plate is washed three times and then incubated with biotinylated anti-mouse IgG1 (diluted by 1:250 in 2% BSA in PBS) for one hour at room temperature with 100 µl per well. After washing the plate a further three times, streptavidin-HRP (1:1000 in 2% BSA in PBS) is added for one hour at room temperature and in the dark. The concentration of the antibodies is determined after adding ABTS and incubating for further 30 minutes and measuring the signal at 405 and 490 nanometers on a spectrophotometer. Based on this determination, a desired amount of the antibodies tested is applied for the further tests.

EXAMPLE 3

Detection of IL-3 by Monoclonal Antibodies in a Western-Blot Assay

For preparing the gel and performing the western-blot analysis, standard methods are used. A 12% PAA resolving gel is poured, overlayed with about 1-2 ml of water and polymerisation conducted for 30 to 45 min until a recognizable "line" is formed. The water is removed, a stacking gel poured onto the resolving gel and a Teflon comb is inserted. Polymerisation is performed for 30 min, then the comb is carefully removed.

Samples of IL-3 are prepared by mixing of recombinant human IL-3 1:1 with Laemmli buffer and heating the samples at 60° C. for 5 min. An amount of 1 µg per lane of IL-3 as well as a usual standard for determining molecule sizes is loaded onto the gel. The gel is then mounted in a SDS-PAGE gel electrophoresis apparatus which already contains a running buffer. The inserted gel is then cautiously overlayed with additional running buffer and electrophoresis performed at 20 to 25 mA with voltage adjusted to infinite for approximately 1.5 hours. When the run is completed, the gel is retrieved from the apparatus and the stacking gel is removed.

Six layers of Whatman paper that has been presoaked in transfer buffer, and a PVDF membrane are cut to fit the size of the gel. The transfer stack is adjusted in the usual way and transfer effected by semi-dry blotting for 40 min at 20-25 mA and voltage adjusted to infinite. The membrane is then incubated overnight at 4° C. on a shaking apparatus with a blocking solution (5% powdered skim milk in PBS) and the membrane washed three times for 5 min each with PBS at room temperature.

Antibody clones are incubated at a concentration of 5 µg/ml in blocking solution for 2 hours at room temperature under agitation on the shaking apparatus. After three washing steps, HRP labelled anti-mouse immune-globulin (1:1000 in blocking solution) is added and incubation is conducted for 1 hour at room temperature while shaking.

After three further washing steps, a detection solution (1:1 mixture of solutions A and B of the Western-blotting Luminal Reagent obtained from NALGENE) is added and incubated for 1 min at room temperature. Films are then adjusted on the membranes with different times of expositions and developed in the dark room.

Figure 2:
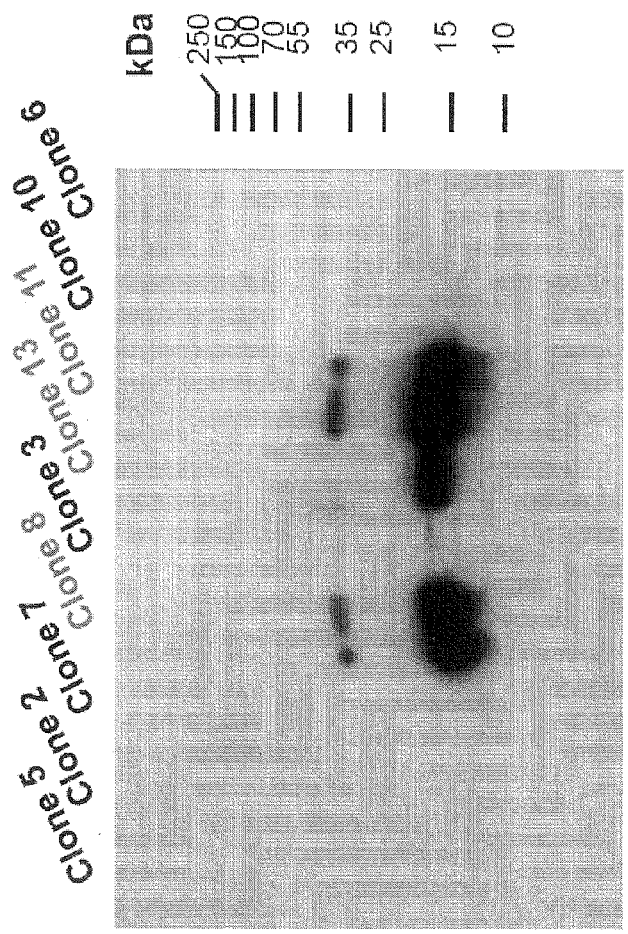
FIG. 2 shows in a Western blot the ability of monoclonal antibodies to bind to IL-3.

FIG. 2 shows the results of binding of antibody clones 2, 3, 5, 6, 7, 8, 10, 11 and 13. Binding to IL-3 at the given concentration was detected for clones 8, 11 and, to a lesser extent, for clone 13.

EXAMPLE 4

Analysis of the IL-3 Affinity and Specificity of Monoclonal Antibodies a) Affinity of the Antibodies for IL3

The affinity of the obtained antibodies for IL-3 was measured in an ELISA assay. ELISA plates were coated overnight with 1 µg/ml of anti-human IL-3 antibody (RD, goat IgG anti-human IL-3 AF-203-NA). For each concentration, duplicates were used (2×12 wells). For this purpose, the first concentration (2 µg/ml) is diluted in PBS, further dilutions are made in PBS containing 2 µg/ml control goat IgG to keep the total concentration of IgG constant. Blocking with 2% BSA is performed for 2 hours at room temperature, followed by 5 washing steps using PBS.

The wells are then incubated with hIL-3 (0.25 µg/ml in PBS) for 2 hours at room temperature, for the control group no hIL-3 is added. After five further washing steps with PBS, the wells are incubated overnight at 4° C. with serial (1:3) dilutions of antibodies clone 8 and 11 obtained in example 1, the antibodies being used in PBS buffer containing 2% BSA and with a starting concentration of 20 µg/ml.

After five further washing steps, bound antibody is detected using goat-anti-mouse-HRP antibody (1:500 in PBS with 2% BSA) and incubation for 1 hour at room temperature. After five further washing steps, ABTS (ROCHE, 1 mg/ml) is added as substrate and the optical density measured in a spectrometer at 405 nm.

Figure 3:
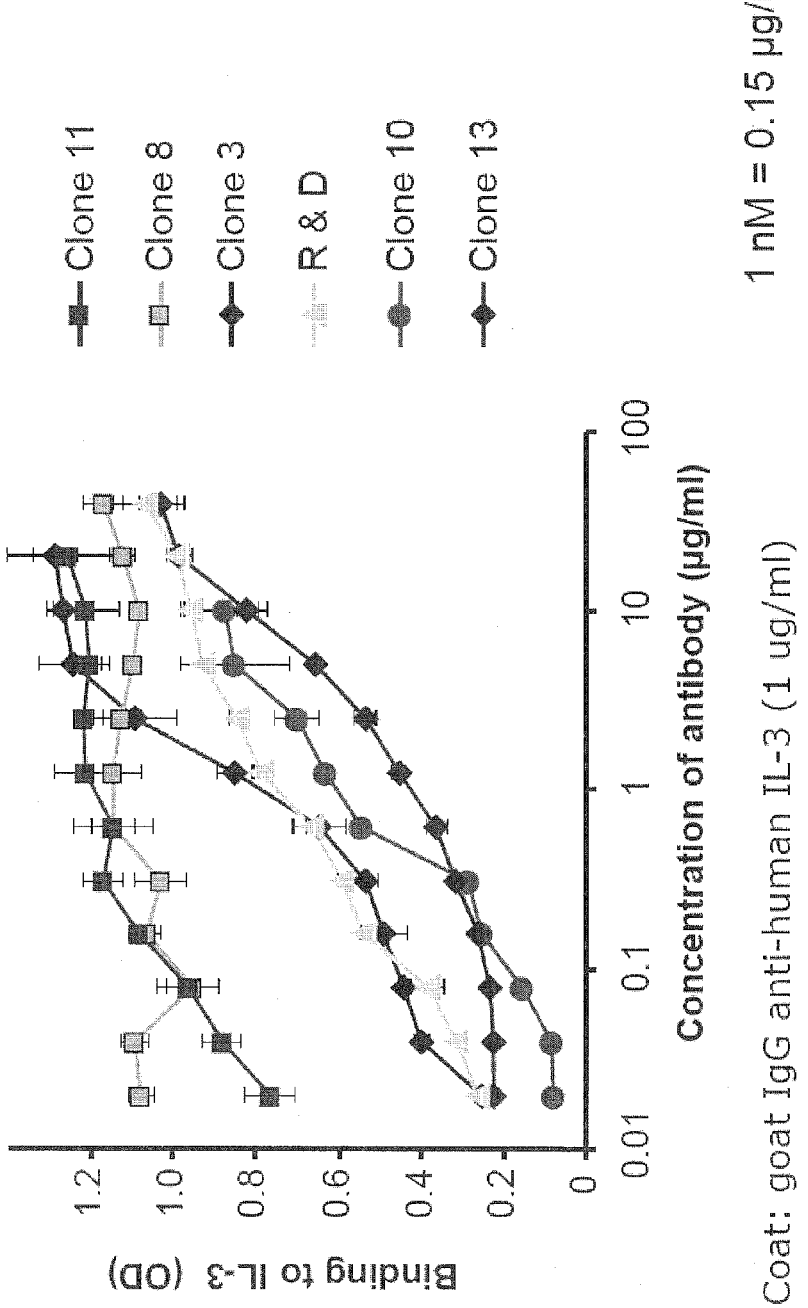
FIG. 3 shows the relative IL-3 affinity of antibodies determined using varying concentrations of antibodies at a constant amount of IL-3 which was bound to the solid phase in an ELISA assay.

FIG. 3 shows the results of tests including antibodies clone 3, 8, 10, 11 and 13. The tests were performed in the manner as described with different concentrations/dilutions of antibodies as shown in the figure I.

b) Cross-reactivity with Other Cytokines

To determine the usefulness of the obtained monoclonal antibodies for diagnostic assays, it is important to be able to exclude cross-reactivities with closely related cytokines which are also present in blood, plasma, serum or other body fluids of patients. To this end, wells of ELISA plates were coated by adding 100 µl/well of human IL-3 (1 µg/ml), GM-CSF (1 µg/ml) or IL-5 (1 µg/ml) in PBS. As negative control PBS was used (100 µl/well). For each tested antibody, different dilutions were tested mandatorily on a common plate with hIL-3, hGM-CSF, hIL-5 and PBS.

The cytokine coated plates were washed three times and blocking performed for 2 hours at room temperature using 2% BSA in PBS. After three further washing steps, antibodies clone 3.47.20, 8.36.38, 10.12.4, 11.14.6, 13.4.4 and just medium (RPMI1640 containing 10% FCS) as control were added at a concentration of 40 µg/ml and 1:5 and 1:25 dilutions thereof in a volume of 100 µl/well and incubated for 1 hour at room temperature. On each plate a negative control is used.

After three washing steps, a secondary HRP-labelled rabbit anti-mouse IgG (DAKO-Cytomation P260 (1:2000 in 2% BSA in PBS, 100 µl/well) was added and the plates incubated at room temperature for 1 hour in the dark. After another three washing steps, ABTS (ROCHE, 1 mg/ml) was added and spectrometry performed at 405 and 490 nm after 30 min.

Figure 4:
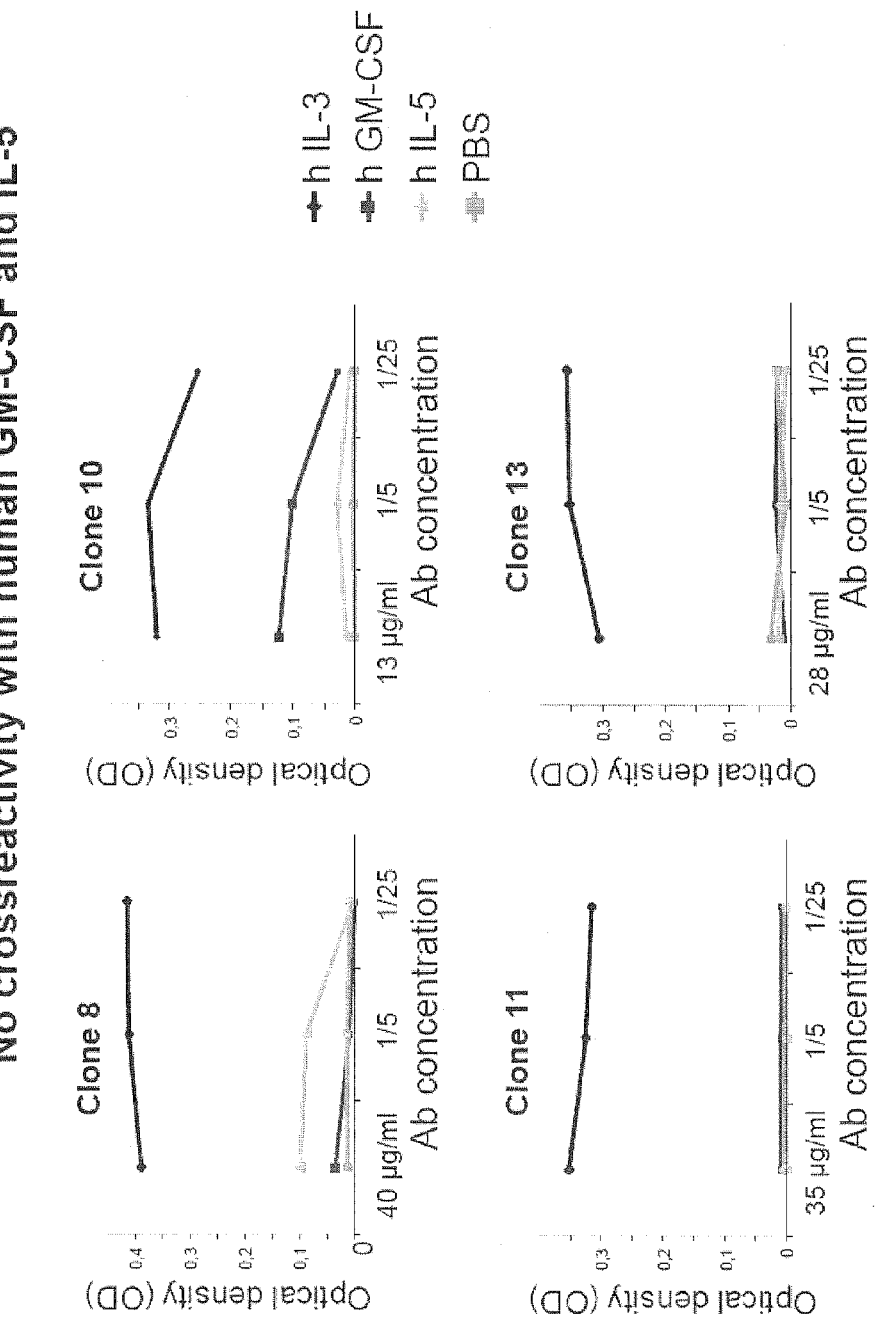
FIG. 4 shows the results of tests performed to detect a possible cross-reactivity of anti-IL-3 antibodies with other human cytokines. In the tests, binding of the antibodies to IL-3, GM-CSF and IL-5 was compared.

The results are shown in FIG. 4 indicating some weak cross-reactivity for clones 8 and 10, but no significant cross-reactivity for clones 11 and 13.

c) Cross-reactivity with IL-3 from Other Species

As a further property of the monoclonal antibodies, their cross reactivity with IL-3 from other species was determined. For a respective assay, the wells of ELISA plates were coated with human, murine, rat and rhesus IL-3 (1 µg/ml) in PBS as well as with PBS as background with 100 µl/well and incubated overnight in a refrigerator. For each antibody, different dilutions were tested mandatorily on a common plate with hIL-3, murine IL-3, rat IL-3, rhesus IL-3 and PBS negative control.

Figure 7:
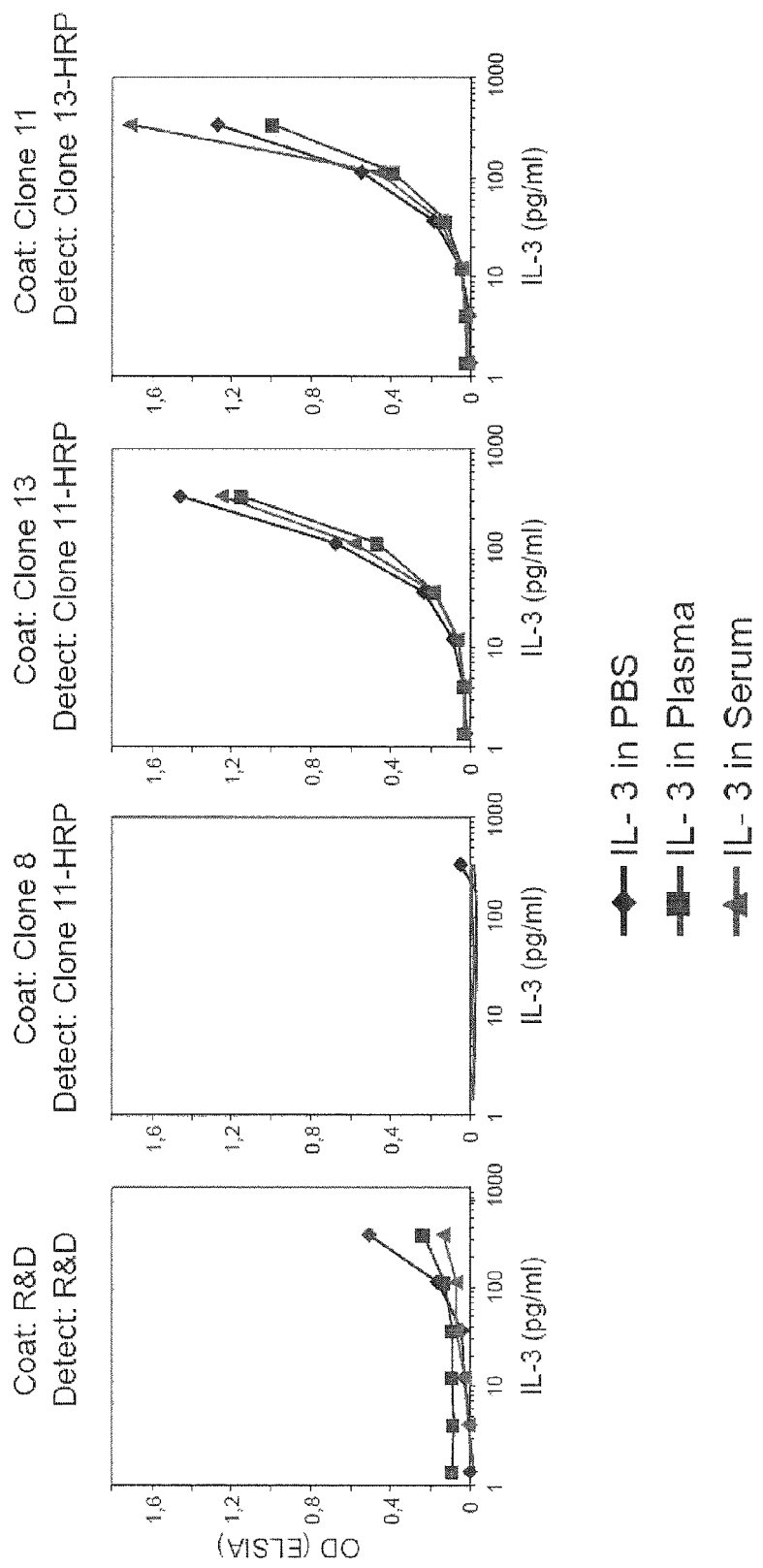
Figure 8:
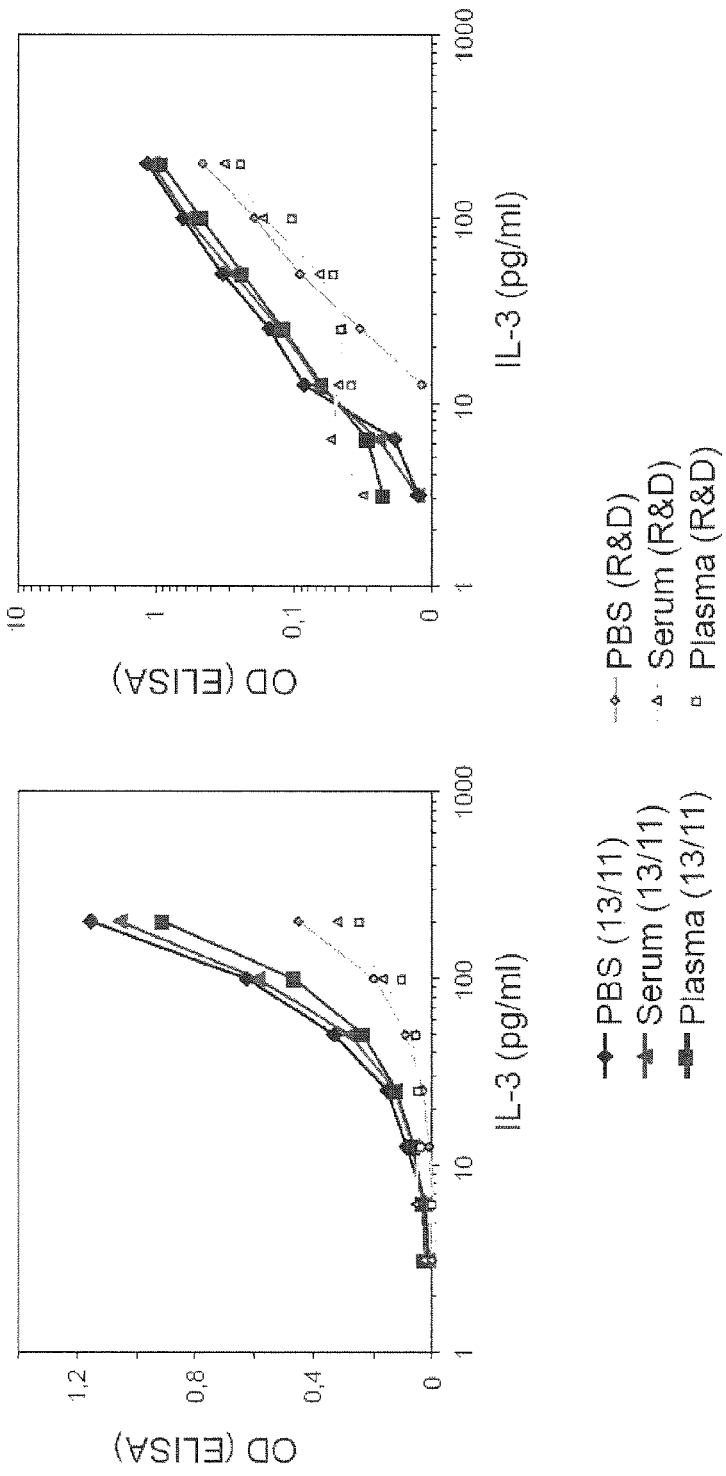
Figure 10:
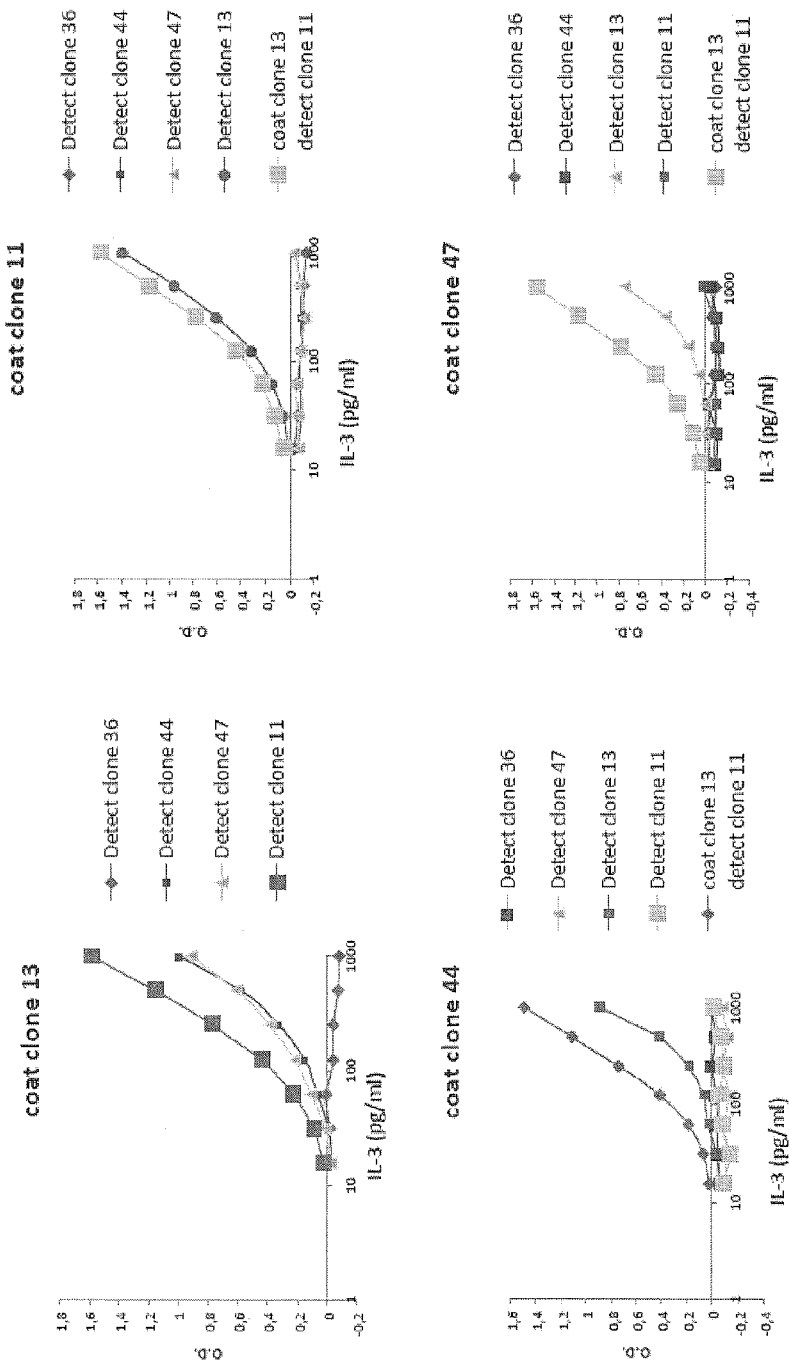
Figure 11:
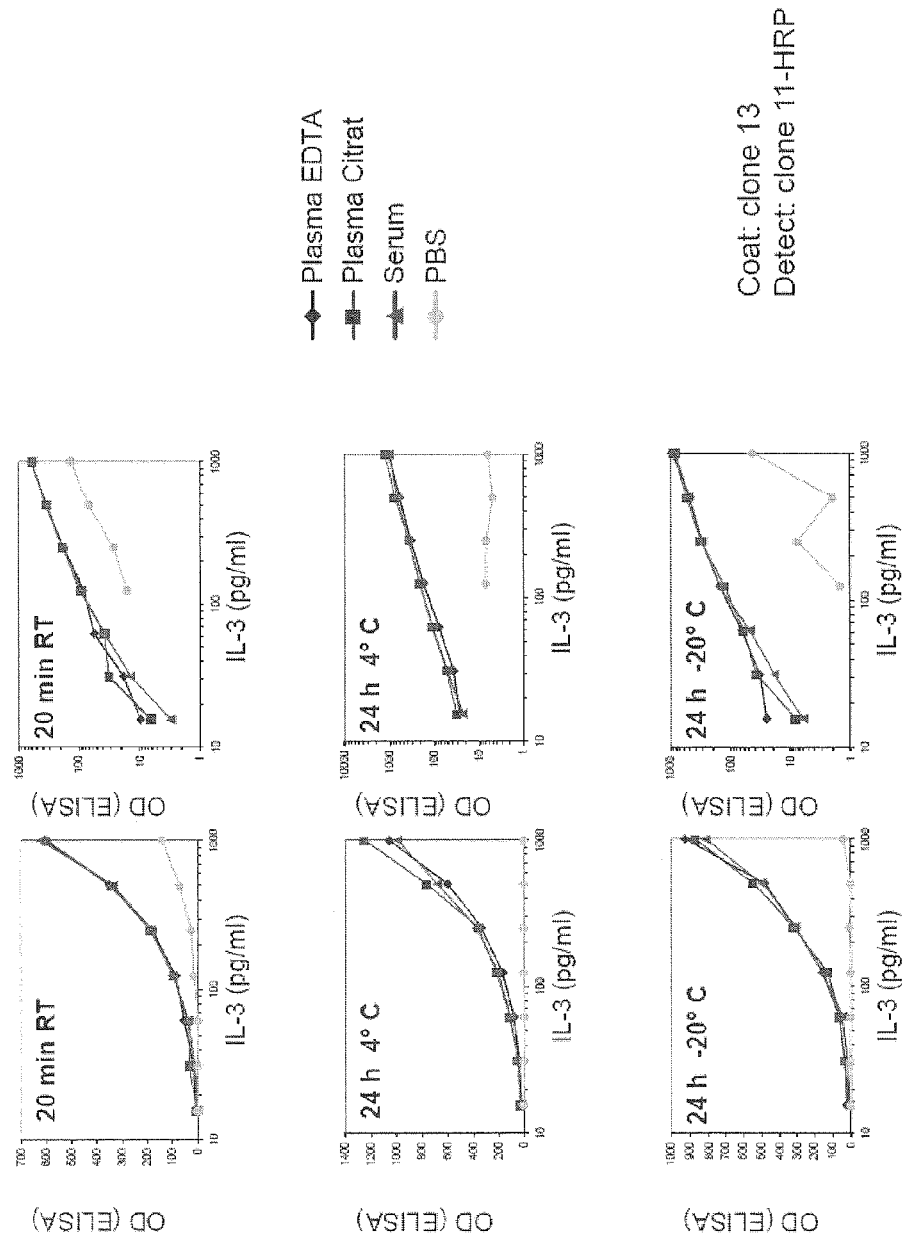

The IL-3 coated plates were washed three times and blocking performed for 2 hours at room temperature with 2% BSA in PBS. After three washing steps, antibody clones 3.47.20, 8.36.38, 10.12.4, 11.14.6, 13.4.4 in certain concentrations as indicated in FIGS. 7 and 8, and 1:5, 1:25 and 1:125 dilutions thereof were added at volumes of 100 µl/well. R&D monoclonal anti-IL-3 antibody clone 4806 (R&D Systems, Inc., catalogue No. MAB203) was used (100 µl/well) in concentrations of 40 µg/ml, 20 µg/ml, 10 µg/ml, 5 µg/ml and 2.5 µg/ml and, as negative control, medium (100 µl/well) without antibody (RPMI 1640 containing 10% FCS) was used. On each plate a negative control was used.

After three washing steps, a secondary HRP-labelled rabbit anti-mouse IgG (DAKO-Cytomation P260 (1:2000 in 2% BSA in PBS, 100 µl/well) was added and the plates incubated at room temperature for 1 hour in the dark. After another three washing steps, ABTS (ROCHE, 1 mg/ml) was added and spectrometry performed at 405 and 490 nm after 30 min.

Figure 5:
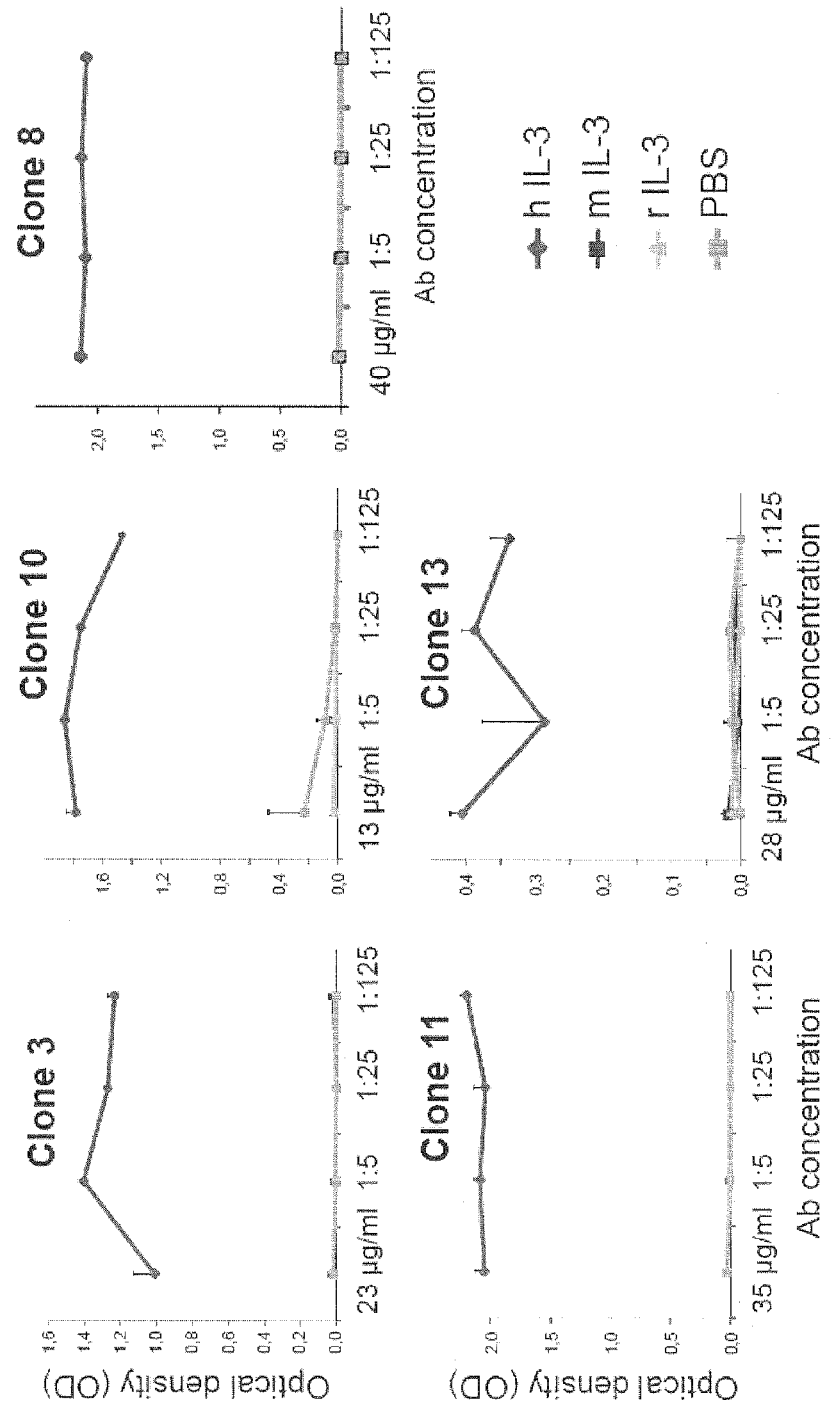
FIGS. 5 and 6 show the results of tests performed to detect possible cross-reactivity of the various anti-IL-3 antibodies with IL-3 from other species. In the test depicted in FIG. 8, also a commercially available anti-IL-3 antibody was included.
Figure 6:
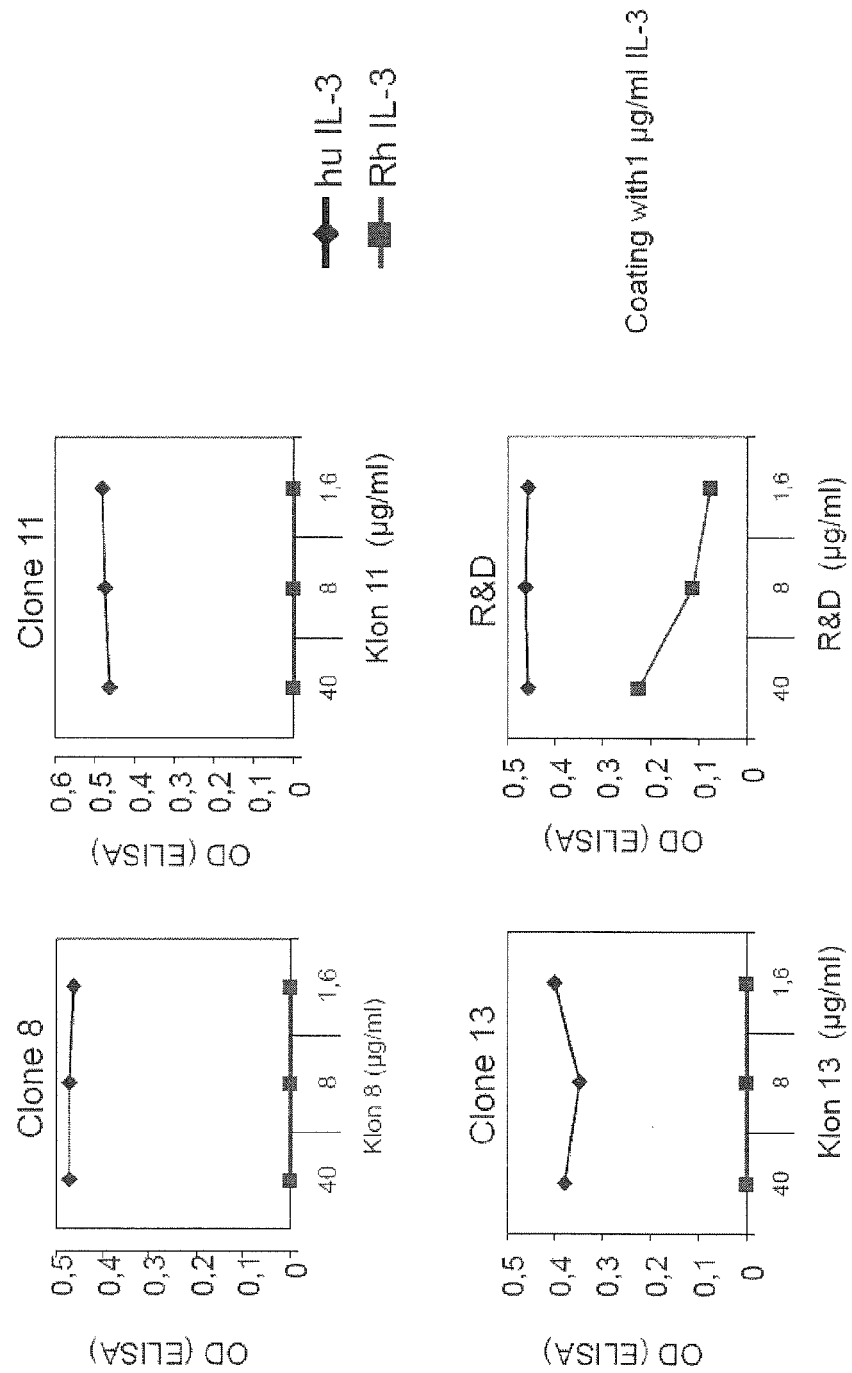

Results are shown in FIGS. 5 and 6, as mentioned above, indicating that albeit a faint cross reactivity of clone 10, none of the antibodies of example 1 showed detectable cross-reactivity. The R&D antibody on the other hand, showed some cross-reaction with rhesus IL-3.

EXAMPLE 5

Development of a Highly Sensitive and Specific ELISA Assay

Anti-IL-3 antibody clones 8, 11, 13 and further antibody clones 44 (44.16.16, DSM ACC3166) and 47 (47.28.15, DSM ACC3167) were analysed for their use in the development of a highly sensitive and specific ELISA assay for the determination of IL-3, especially for diagnostic purposes in blood, plasma or serum, as well as other body fluids.

To this end, ELISA plates were incubated with 5 µg/ml of anti-IL-3 antibody overnight at room temperature to coat the plates. After three washing steps, blocking is performed using 1% BSA in PBS at 100 µl/well for 1 hour at room temperature. After further three washing steps, samples are incubated with 60 µl/well of IL-3 in various concentrations in PBS, plasma and serum. After another three washing steps, detection of solid-phase bound IL-3 is performed by adding 60 µl/well of a different and HRP labelled anti-IL-3 antibody at a concentration of 400 ng/ml and incubation for 2 hours at room temperature, followed by three washing steps and addition of TMB buffer (10 ml TMB buffer, 1 tablet of TMB, 3 µl $H_2O_2$) (0.1 mg/ml, SIGMA-ALDRICH).

The reaction is stopped by adding 100 µl/well of $H_2SO_4$ (12.5% in $H_2O$). The results are obtained by spectrometry at 450 nm and shown in FIGS. 7 to 10.

Labelling of the anti-IL3 antibody clones was performed using the Lightning-Link HRP Conjugation Kit (Innova Biosciences) using the following protocol: For each of the purified antibody clones 8, 11, 13, 44 and 47 100 µl solutions with a concentration of 1 µg/µl (in PBS) were produced. To each antibody solution, 10 µl of LL-modifying reagent were added and the obtained solution mixed carefully. For each antibody solution a Lightning Link mix bottle (100 µg reagent) was opened and the antibody solution including the LL-modifying agent added directly onto the reagent powder. Mixing was performed very cautiously by up- and down-pipetting of the solution. The lid was readjusted on the bottle of the Lightning Link mix and the bottles incubated for 3 hours at room temperature whereupon 10 µl LL-quencher reagent were added and incubated for a further 30 min at room temperature. After this treatment the antibodies were stored at −20° C. for further use.

As a comparative assay, analogue tests were performed using the Quantikine Human IL-3 ELISA test kit provided by R&D Systems, Inc., Catalogue No. Dy 203.

Figure 12:
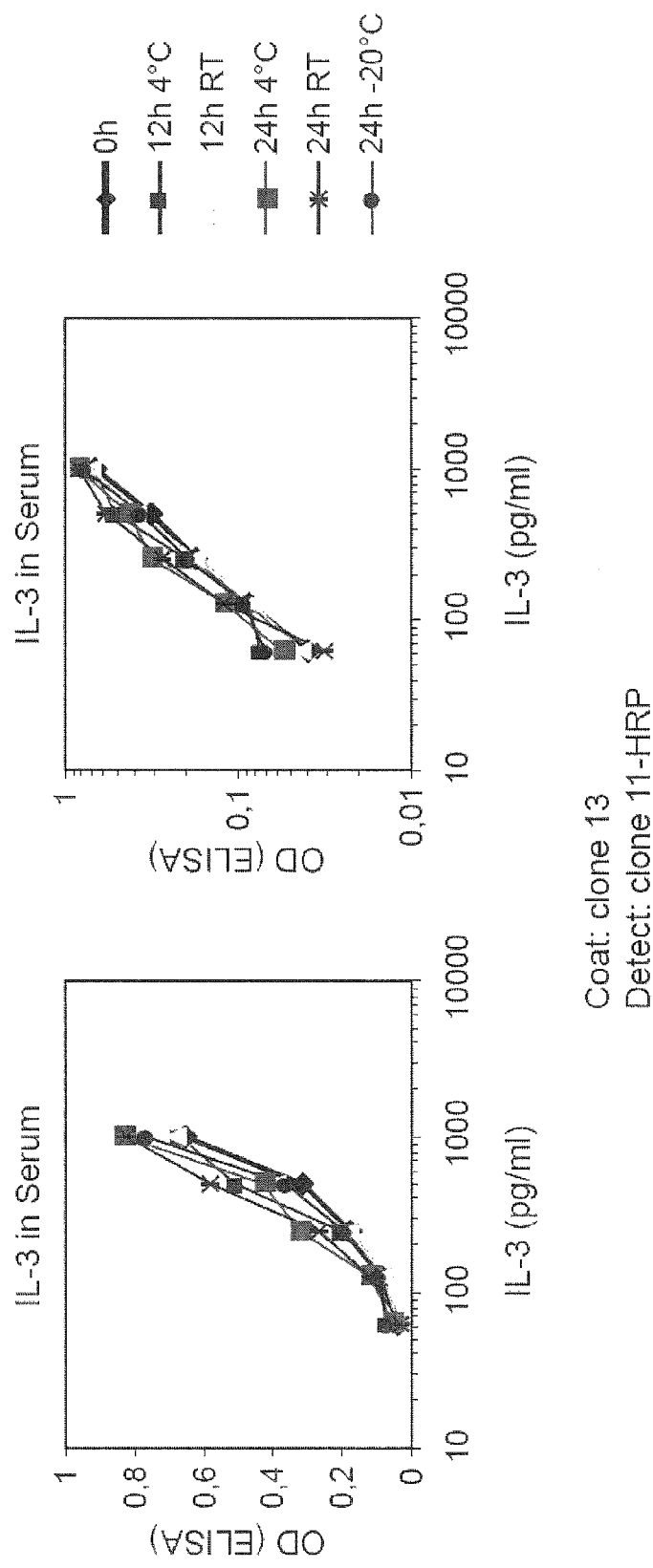
Figure 13:
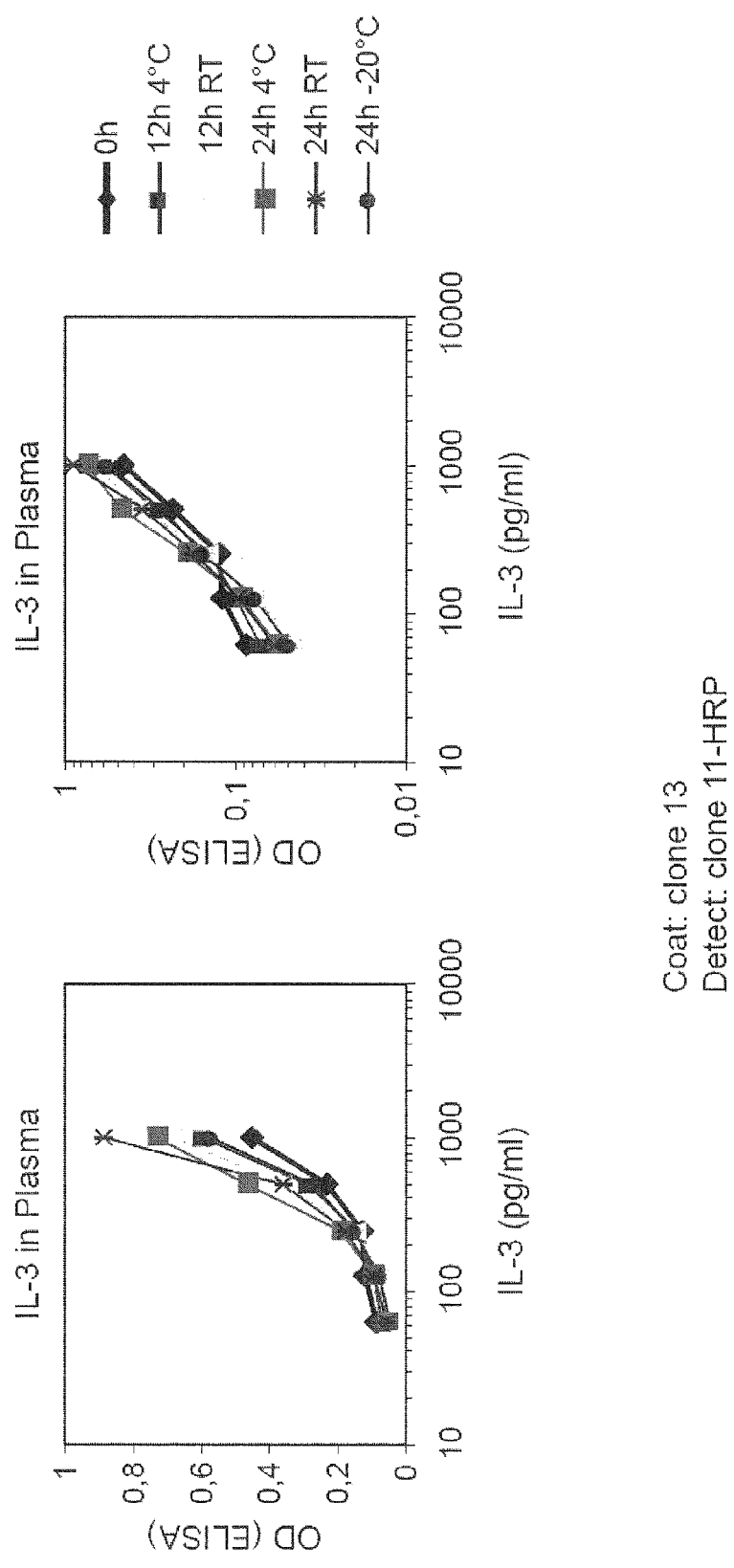
Figure 14:
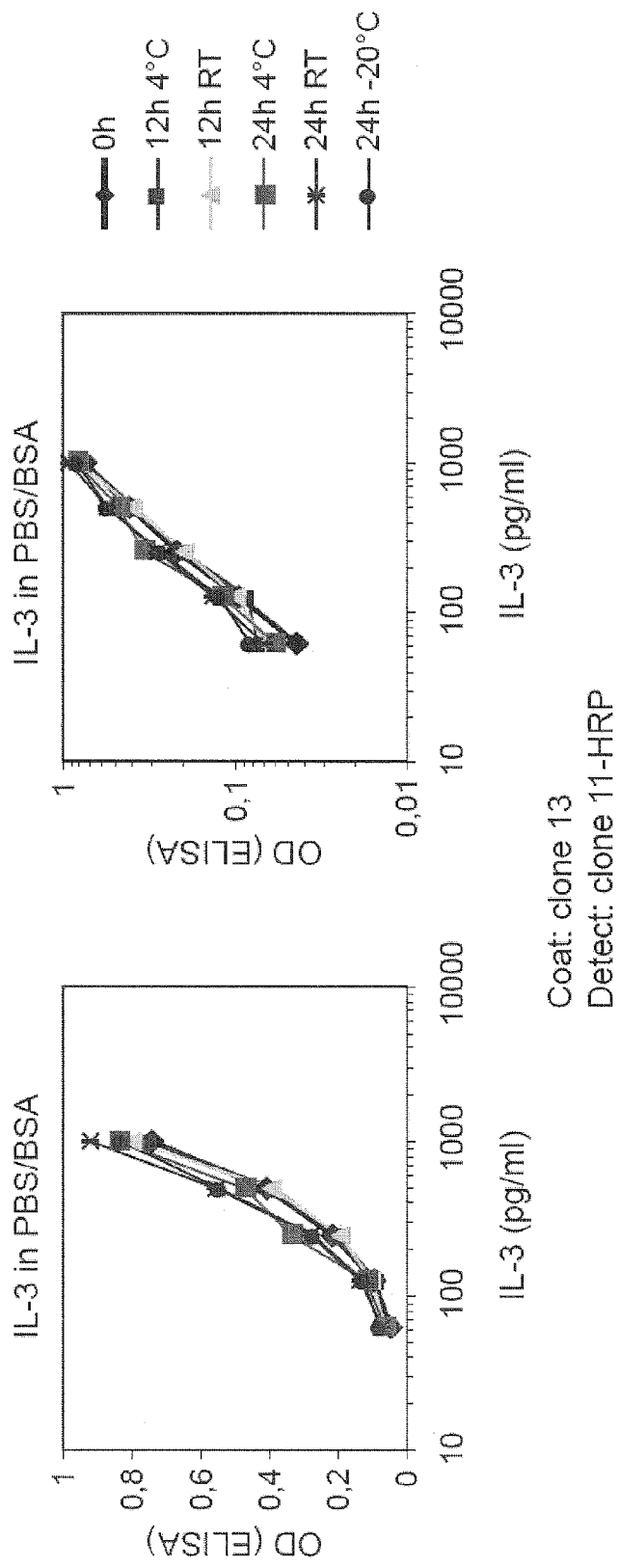

The results of this experiment are shown in FIG. 7 to 10 and indicate that antibody clone 8 is not suitable as either coating or detection antibody, whereas antibody clones 11 and 13 are both suitable as coating and detection antibodies and the best results are achieved using clone 13 as coating and clone 11-HRP as detection antibody. It is furthermore observed that the commercially available IL-3 ELISA test kit obtainable from R&D Systems shows a remarkably lower sensitivity as an ELISA test kit according to the present invention with antibody clones 13 and 11 (FIG. 7). It was also observed that the IL-3 ELISA test kit of R&D Systems showed high background signals and therefore was not sufficiently reliable and sensitive when plasma or serum samples are used. An inventive test kit with clones 13/11, on the other hand, retained the same sensitivity as when using PBS or PBS/BSA samples also for plasma and serum (comparison shown in FIG. 10). Tests performed with different plasma samples (Plasma EDTA, Plasma Citrat) and serum could also be shown to be stable for at least 24 hours at room temperature (FIG. 11) and there was also no detectable signal loss after freezing and thawing of the samples (FIGS. 12-14).

EXAMPLE 6

Analysis of IL-3 Level in Plasma of Patients

An ELISA assay with clone 13 as coating and clone 11-HRP as detection antibody was performed for patients with inflammatory joint diseases. Test conditions and reagents were as described in Example 7. The results are shown in FIG. 15.

It was observed that in patients with non-active RA (DAS28<2.6, N=9) the mean plasma level of IL-3 was significantly lower (12 pg/ml) than for patients with active RA (DAS28≥2.6, N=45; IL-3=73 pg/ml). For patients suffering from a different form of arthritis (non-rheumatoid arthritis, n=10), also significantly lower mean IL-3 plasma levels (IL-3=1 pg/ml) were observed than for patients with active RA.

Remarkably, there were two groups of patients with active RA (DAS≥2.6). About half of the patients (N=21) showed very low IL-3 plasma levels (mean value IL-3=1.3 pg/ml, SEM (standard error of the mean)=0.27 pg/ml), whereas the second group (N=24) showed very high IL-3 levels (mean value IL-3=136 pg/ml, SEM=35 pg/ml). The ability to perform the test according to the present invention and to gain reliable and specific information about the IL-3 levels in the patients allows for a stratification of active-RA patients for a therapeutic IL-3 blocking treatment into sub-groups with high and with low IL-3 levels. Patients with high IL-3 levels can be considered as a target group that will greatly benefit from such treatment.

For a further experiment, random plasma samples from patients treated at the University Hospital Regensburg were analyzed. The diagnosis of these patients was not known as the samples were analyzed in an anonymous way. The data obtained are shown in FIG. 16 and indicate that only a very low percentage of patients (4.7%) treated at the University Hospital express high levels of IL-3 while most of the patients express no IL-3 or very low levels thereof.

In further experiments plasma IL-3, IL-6 and TNF-α levels have been analysed in patients suffering from arthritis/arthralgia (no rheumatoid arthritis; n=87) or from rheumatoid arthritis (n=108) (FIG. 17). The obtained data clearly demonstrate that IL-3 but not IL-6 or TNF-α can separate between RA and non-RA types of arthritis.

Within the group of RA patients it was found that IL-3 and IL-6 but not TNF-α levels were strongly increased in patients with active RA (DAS28 >2.6; n=93) compared to patients with non-active RA (DAS28≤2.6; n=15). Still, the IL-6 levels were clearly decreased in comparison to the IL-3 levels (FIG. 18).

As shown in FIG. 19 >60% of the patients not responding to DMARDs/biologicals express high IL-3 levels. Among those patients that did not respond to current therapies patients with high IL-3 levels were more frequent. These patients would qualify for treatment with anti-IL-3 antibodies since the data indicate that patients with high IL-3 levels obviously do not respond to other kinds of therapies like, e.g., DMARDs or biologicals.

The invention claimed is:

1. A nucleic acid encoding anti-IL3 antibody clone 13 produced by the hybridoma deposited as Deutsche Sammlung von Mikroorganism (DSM) ACC3164.

2. A vector comprising the nucleic acid of claim 1.

3. A host cell comprising the vector of claim 2.

* * * * *

SEQUENCE LISTING

<160> NUMBER OF SEQ ID NOS: 2

<210> SEQ ID NO 1
<211> LENGTH: 133
<212> TYPE: PRT
<213> ORGANISM: Homo sapiens
<220> FEATURE:
<221> NAME/KEY: misc_feature
<222> LOCATION: (1)..(133)
<223> OTHER INFORMATION: Human IL-3 (without signal peptide)

<400> SEQUENCE: 1

Ala Pro Met Thr Gln Thr Thr Pro Leu Lys Thr Ser Trp Val Asn Cys
 1               5                  10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
        35                  40                  45

Met Glu Asn Asn Leu Arg Arg Pro Asn Leu Glu Ala Phe Asn Arg Ala
    50                  55                  60

Val Lys Ser Leu Gln Asn Ala Ser Ala Ile Glu Ser Ile Leu Lys Asn
65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
    130

<210> SEQ ID NO 2
<211> LENGTH: 4
<212> TYPE: PRT
<213> ORGANISM: Homo sapiens
<220> FEATURE:

```
<221> NAME/KEY: misc_feature
<222> LOCATION: (1)..(4)
<223> OTHER INFORMATION: Human IL-3 epitope

<400> SEQUENCE: 2

Ser Trp Val Asn
1
```